United States Patent
Tian et al.

(10) Patent No.: US 11,634,693 B2
(45) Date of Patent: Apr. 25, 2023

(54) L-GLUTAMATE DEHYDROGENASE MUTANT AND APPLICATION THEREOF

(71) Applicant: ABIOCHEM BIOTECHNOLOGY CO., LTD, Shanghai (CN)

(72) Inventors: Zhenhua Tian, Shanghai (CN); Zhanbing Cheng, Shanghai (CN); Shaonan Ding, Shanghai (CN); Wenxuan Xu, Shanghai (CN); Ruru Wang, Shanghai (CN); Qi Jiao, Shanghai (CN); Yao Huang, Shanghai (CN)

(73) Assignee: ABIOCHEM BIOTECHNOLOGY CO., LTD, Shanghai (CN)

(*) Notice: Subject to any disclaimer, the term of this patent is extended or adjusted under 35 U.S.C. 154(b) by 67 days.

(21) Appl. No.: 17/043,450

(22) PCT Filed: Apr. 3, 2019

(86) PCT No.: PCT/CN2019/081172
§ 371 (c)(1),
(2) Date: Sep. 29, 2020

(87) PCT Pub. No.: WO2019/192505
PCT Pub. Date: Oct. 10, 2019

(65) Prior Publication Data
US 2021/0024902 A1     Jan. 28, 2021

(30) Foreign Application Priority Data
Apr. 3, 2018 (CN) ..................... 201810291900.4

(51) Int. Cl.
*C12N 9/06* (2006.01)
*C12P 13/04* (2006.01)

(52) U.S. Cl.
CPC ............ *C12N 9/0028* (2013.01); *C12P 13/04* (2013.01)

(58) Field of Classification Search
None
See application file for complete search history.

(56) References Cited

U.S. PATENT DOCUMENTS

| | | | |
|---|---|---|---|
| 4,389,488 A | 6/1983 | Grabley et al. | |
| 5,221,737 A | 6/1993 | Bartsch et al. | |
| 6,936,444 B1 | 8/2005 | Bartsch | |
| 9,834,802 B2 | 12/2017 | Green et al. | |
| 2017/0240868 A1* | 8/2017 | Chen | C12Y 104/01004 |
| 2020/0102546 A1 | 4/2020 | Yang et al. | |

FOREIGN PATENT DOCUMENTS

| | | |
|---|---|---|
| CN | 1053669 C | 6/2000 |
| CN | 1284858 C | 11/2006 |
| CN | 102199578 A | 9/2011 |
| CN | 102199578 B | 6/2013 |
| CN | 106978453 A | 7/2017 |
| CN | 108588045 A | 9/2018 |
| CN | 110055289 A | 7/2019 |
| CN | 110343676 A | 10/2019 |
| EP | 0344683 A | 12/1989 |
| EP | 0382113 A | 8/1990 |
| EP | 1177310 A1 | 2/2002 |
| WO | 9523805 A1 | 9/1995 |
| WO | 2016050959 A2 | 4/2016 |

OTHER PUBLICATIONS

Singh et al., Curr. Protein Pept. Sci. 18:1-11, 2017 (Year: 2017).*
Zhang et al., Structure 26:1474-1485, 2018 (Year: 2018).*
Yin et al., Appl. Microbiol. Biotechnol. 102:4425-4433, 2018 (Year: 2018).*
Schultz et al., Proteins Structure and Function, pp. 521-528, Plenum Press, New York, 1987 (Year: 1987).*
UniProt Database Accession No. Q9C8I0, Jan. 2022, 2 pages (Year: 2022).*
UniProt Database Accession No. Q9RXZ6, Dec. 2020, 2 pages (Year: 2020).*
Betts et al., Bioinformatics for Geneticists, Chapter 14, Amino Acid Properties and Consequences of Substitutions, pp. 289-316, 2003 (Year: 2003).*
Extended European Search Report dated Dec. 22, 2021 issued in European Application No. 19780685.4, 20 pages.
Xinjian Yin, et al., "Efficient reductive amination process for enantioselective synthesis of L-phosphinothricin applying engineered glutamate dehydrogenase", Applied Microbiology and Biotechnology, Springer Berlin Heidelberg, vol. 102, No. 10, Mar. 16, 2018, pp. 4425-4433.
Takeo Tomita, et al., "Crystal structure of the 2-iminoglutarate-bound complex of glutamate dehydrogenase from Corynebacterium glutamicum", FEBS Letters, vol. 591, No. 11, May 25, 2017, pp. 1611-1622.

(Continued)

Primary Examiner — David Steadman
(74) Attorney, Agent, or Firm — Foley & Lardner LLP

(57) ABSTRACT

Provided are an L-glutamate dehydrogenase mutant and an application thereof, the mutant mutating the amino acid residue A at position 166 and/or the amino acid residue V at position 376 shown in SEQ ID NO. 1 into a hydrophilic or small sterically hindered amino acid residue, the application performing an amination reaction of 2-oxo-4-(hydroxymethylphosphinyl)butyrate in the presence of an L-amino acid dehydrogenase mutant, an inorganic amino donor, and a reduced coenzyme NADPH, and performing an acidification reaction on the obtained L-glufosinate salt to obtain L-glufosinate. Compared to wild L-glutamate dehydrogenase, the present L-glutamate dehydrogenase mutant has a higher concentration of substrates that can be catalysed when preparing L-glufosinate, thereby increasing the efficiency of the action of the enzyme and reducing reaction costs.

9 Claims, 4 Drawing Sheets

Specification includes a Sequence Listing.

(56) References Cited

OTHER PUBLICATIONS

Feng Geng, et al., "Reengineering substrate specificity of *E. coli* glutamate dehydrogenase using a position-based prediction method", Biotechnology Letters, Kluwer Academic Publishers, Dordrecht, vol. 39, No. 4, Feb. 9, 2017, pp. 599-605.
International Search Report dated Jul. 10, 2019 issued in International Patent Application No. PCT/CN2019/081172, with English translation, 6 pages.
Written Opinion of the International Searching Authority dated Jul. 10, 2019 issued in International Patent Application No. PCT/CN2019/081172, with English translation, 13 pages.
Elbrghathi, Abdelhamid, "Structural studies on dehydrogenases," Doctoral thesis, University of Sheffield, Jul. 2014, 232 pages.

* cited by examiner

L-GLUTAMATE DEHYDROGENASE MUTANT AND APPLICATION THEREOF

CROSS-REFERENCE TO RELATED APPLICATIONS

The present application is a 371 of PCT/CN2019/081172, filed Apr. 3, 2019, which is based upon and claims priority to Chinese patent application CN201810291900.4, filed on Apr. 3, 2018, both of which are hereby incorporated by reference in their entireties.

SEQUENCE LISTING

The instant application contains a Sequence Listing which is being submitted in ASCII format via EFS-WEB and is hereby incorporated by reference in its entirety. Said ASCII copy, created on Sep. 16, 2020, is named P20414069USSEQ.txt and is 98 kb.

TECHNICAL FIELD

The present invention relates to the field of biotechnology, particularly, relates to an L-glutamate dehydrogenase mutant and an application thereof.

BACKGROUND ARTS

Glufosinate is a broad-spectrum contact herbicide developed by Hoechst Inc. in the 1980s. At present, three major herbicides in the world are glyphosate, glufosinate and paraquat. Compared with glyphosate and paraquat, glufosinate has excellent herbicidal properties and less side effects. Glufosinate has two optical isomers, namely D-glufosinate and L-glufosinate, respectively. However, only L-glufosinate has herbicidal activity. Therefore, the development of a method for preparing L-glufosinate is of great significance for improving the atomic economy, reducing the cost of use and relieving environmental pressure.

At present, the method for preparing L-Glufosinate mainly includes chiral resolution, chemical synthesis and biocatalysis.

Chiral resolution such as CN1053669C disclosed a method for preparing L-glufosinate by using quinine alkaloids as resolving agents, recrystallizing L-glufosinate quinine salt, which was then neutralized with acid. Meanwhile, 5-nitrosalicylaldehyde or 3, 5-dinitrosalicylaldehyde was used as a racemization reagent to racemize unreacted D-glufosinate to give DL-glufosinate, which was used for resolution reaction subsequently. However, this method requires expensive chiral resolution reagents and multi-step recrystallization, which is cumbersome and not ideal.

Chemical synthesis such as U.S. Pat. No. 6,936,444 disclosed that 2-acetamido-4-(hydroxymethylphosphinyl)-2-butenoic acid is asymmetrically hydrogenated by ruthenium catalysts to give L-2-acetamido-4-(hydroxymethylphosphinyl))-2-butyric acid, which can be deacetylated subsequently to give L-glufosinate. This method requires expensive metal catalysts, which increases the cost of synthesis, and produces heavy metal residues, thereby seriously polluting the environment.

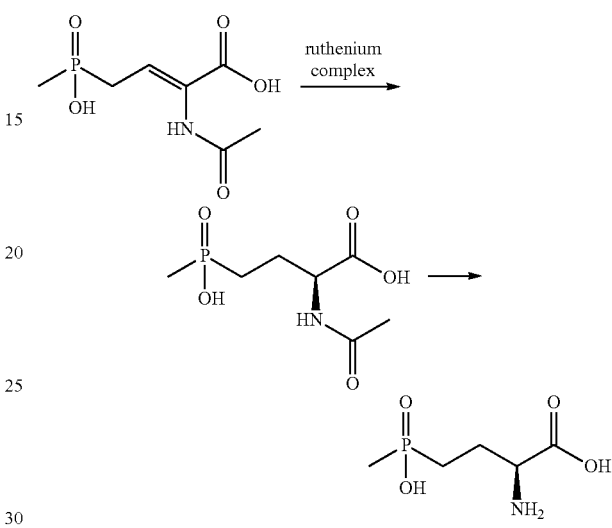

Compared with chiral resolution and chemical synthesis, biocatalysis has the advantage of strong specificity and mild reaction conditions, etc., and is a superior method for the production of L-glufosinate.

U.S. Pat. No. 4,389,488A described a method for producing L-glufosinate by using N-phenylacetyl-DL-glufosinate as substrate, and penicillin-G-acylase derived from *Escherichia coli* as catalyst. However, the synthesis cost of phenylacetyl glufosinate is relatively high, and a mixed solution of L-glufosinate, N-phenylacetyl-D-glufosinate and phenylacetic acid is obtained after the reaction, thereby requiring a strong acid cation exchange resin to separate L-glufosinate from the mixture, so the operation is complicated.

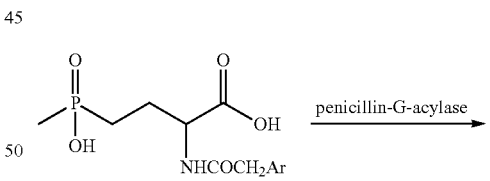

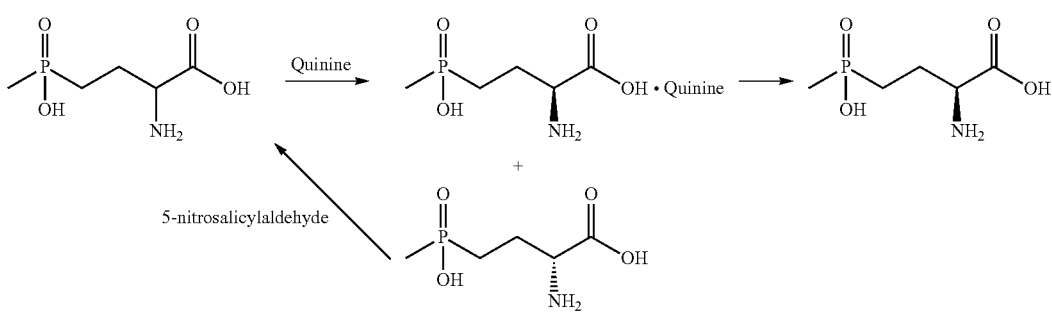

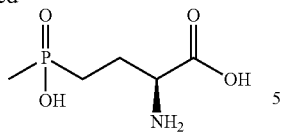
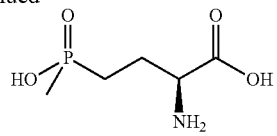

EP0382113A described a method for preparing L-glufosinate by catalytically cleaving the carboxylate of N-acetyl-glufosinate with acyltransferase, but enzyme therein is not specific to free N-acetyl-glufosinate, therefore, it's necessary for N-acetyl-glufosinate to be esterified, which increases the reaction steps and correspondingly increases the cost of production.

In other methods, 2-oxo-4-(hydroxymethyl phosphinyl) butyric acid (PPO) was used as substrate to prepare L-glufosinate by transaminase catalysis. Among them, U.S. Pat. No. 5,221,737A and EP0344683A described methods for preparing L-glufosinate from corresponding keto acid 4-(hydroxymethylphosphinyl)-2-oxobutyric acid by transaminase derived from *Escherichia coli*, using glutamine acid as amino donor. The reaction system needs equal or excessive of glutamic acid as amino donor, which makes it difficult to purify the product. CN1284858C improved the above methods by using aspartic acid as amino donor, and giving L-glufosinate from corresponding keto acid 4-(hydroxymethylphosphinyl)-2-oxobutyric acid by aspartate aminotransferase, in which aspartic acid is converted to oxaloacetic acid. Oxaloacetic acid is unstable in aqueous medium and spontaneously decarboxylated to pyruvate, which can be removed by enzymatic reaction, making the reverse reaction impossible. Therefore, the reaction requires only equimolar amino donor and amino acceptor. However, the majority of the amino donors used in the method of using transaminase are amino acids, which has a relatively high cost.

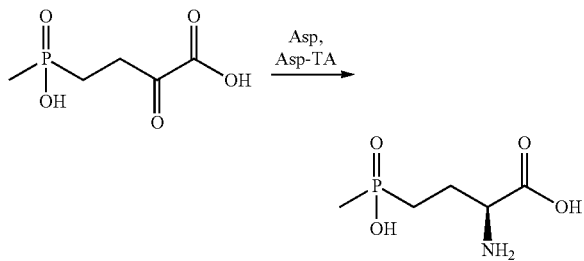

In addition, there is method for preparing L-glufosinate using 2-oxo-4-(hydroxymethylphosphinyl) butyric acid (PPO) as substrate and amino acid dehydrogenase as catalyst. CN106978453A, for instance, used inorganic amino groups as donor, which makes the separation of the product simple and reduces the cost. However, the concentration range of substrate catalyzed by the enzyme in CN106978453A is only 10-100 mM, and the catalytic efficiency of amino acid dehydrogenase is limited.

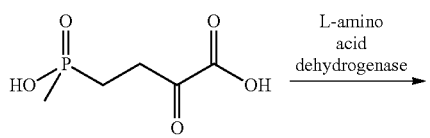

Content of the Present Invention

The technical problem to be solved by the present invention is the existing defect that L-glutamate dehydrogenase has a low catalytic efficiency in preparing L-glufosinate. Therefore, the present invention provides an L-glutamate dehydrogenase mutant and an application thereof in preparing L-glufosinate or salts thereof. Compared with wild-type L-glutamate dehydrogenase, the present L-glutamate dehydrogenase mutant can catalyze a higher concentration of substrates when preparing L-glufosinate, thereby increasing the efficiency of the enzyme and reducing reaction costs, which is advantageous to industrial production.

The source of wild-type L-glutamate dehydrogenase used in the present invention is *Corynebacterium glutamicum*, with a PDB number of 5IJZ. The wild-type L-glutamate dehydrogenase consists of 447 amino acid residues, and its enzyme activity is very low when catalyzing the substrate 2-oxo-4-(hydroxymethylphosphinyl) butyric acid (PPO), which is not suitable for industrial production. The inventors performed saturation mutagenesis screening on different amino acid positions of the wild-type enzyme with PPO as substrate, and found that some mutants at positions A166, V376, or T196 significantly improved the enzyme activity with PPO as new substrate. Furthermore, combinations of these site mutations were conducted to construct a mutant library, from which the L-glutamate dehydrogenase mutants of the present invention are screened out.

The first technical solution that solves the above-mentioned technical problems in the present invention is provided as follows: an L-glutamate dehydrogenase mutant comprising a sequence obtained by mutating amino acid residue A at position 166 and/or amino acid residue Vat position 376 of SEQ ID NO. 1 to an amino acid that is basic, hydrophilic or small sterically hindered, Wherein, the sequence of the L-glutamate dehydrogenase mutant is neither the sequence of SEQ ID NO. 8, nor the sequence of SEQ ID NO. 22.

Preferably, the L-glutamate dehydrogenase mutant has an activity of catalyzing 2-oxo-4-(hydroxymethylphosphinyl) butyric acid or salts thereof.

According to the present invention, the amino acid that is basic, hydrophilic or small sterically hindered means that compared with the amino acid residues of wild-type sequence, the mutated amino acid residues are more basic, more hydrophilic or less sterically hindrance. In general, as long as mutated amino acid residue at either position 166 or 376 has already satisfied the above criteria, the mutated amino acid residue at the other position need not be strictly limited to have the above criteria. The amino acids can be modified or unmodified natural amino acids; the present invention takes natural amino acids as an example.

Preferably, the amino acid residue A at position 166 can be mutated to G, C, E, H or T, and/or the amino acid residue V at position 376 can be mutated to A, E, G, P, Q or S.

More preferably, the mutant of the present invention also comprises mutating the amino acid residue T at position 196 of SEQ ID NO. 1 to V, S or C.

Even more preferably, the amino acid residue A at position 166 is mutated to G, H or T, the amino acid residue V at position 376 is mutated to E, G, Q or S, and/or the amino acid residue T at position 196 is mutated to S or C.

In a preferred embodiment of the present invention, the amino acid residue A at position 166 is mutated to T, or the amino acid residue V at position 376 is mutated to G.

The above-mentioned capital English single letters represent amino acids as well known to those skilled in the art. According to the present invention, the letters herein represent the corresponding amino acid residues.

Preferably, the L-glutamate dehydrogenase mutant consists of an amino acid sequence of SEQ ID NO. 10, SEQ ID NO. 12, SEQ ID NO. 14, SEQ ID NO. 16, SEQ ID NO. 18, SEQ ID NO. 20, SEQ ID NO. 24, SEQ ID NO. 26, SEQ ID NO. 28, SEQ ID NO. 30, SEQ ID NO. 32, SEQ ID NO. 34, SEQ ID NO. 36 or SEQ ID NO. 38.

Preferably, the nucleotide sequence of the L-glutamate dehydrogenase mutant is set forth in SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37 or SEQ ID NO. 39.

The second technical solution that solves the above-mentioned technical problems in the present invention is provided as follows: an isolated nucleic acids encoding the L-glutamate dehydrogenase mutant of any one of claims 1 to 4.

Preferably, the nucleotide sequence encoding the nucleic acids is set forth in SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37 or SEQ ID NO. 39.

The third technical solution that solves the above-mentioned technical problems in the present invention is provided as follows: a recombinant expression vector comprising the nucleic acids described above.

The fourth technical solution that solves the above-mentioned technical problems in the present invention is provided as follows: a transformant comprising the nucleic acids or the recombinant expression vector described above.

The fifth technical solution that solves the above-mentioned technical problems in the present invention is provided as follows: a method for preparing L-glufosinate salt, which comprises the following steps: 2-oxo-4-(hydroxymethylphosphinyl) butyrate is subjected to an amination reaction to give an L-glufosinate salt in the presence of a reaction solvent, an L-glutamate dehydrogenase mutant, an inorganic amino donor and a reduced coenzyme NADPH (nicotinamide adenine dinucleotide phosphate).

In the preparation method, except for the L-glutamate dehydrogenase mutant which is obtained by the present invention, the other raw materials, reaction steps and conditions can be conventional in the art. For details, please refer to the above-mentioned CN106978453A and the patent application of the applicant with application number CN201810162629.4, and the entire contents of these documents are incorporated by reference herein.

The method for preparing the L-glufosinate salt can further comprises the following steps: a D-glufosinate salt is subjected to an oxidation reaction to give the 2-oxo-4-(hydroxymethylphosphinyl) butyrate in the presence of D-amino acid oxidase (DAAO).

In the oxidation reaction, the cation of the D-glufosinate salt can be a cation of conventional in the art, such as ammonium ion, sodium ion and/or potassium ion. It can also be any cation of the buffer used.

In the oxidation reaction, the D-glufosinate salt can have a form of existing alone, or, coexisting with L-glufosinate salt (the L-glufosinate salt can not react at this time), e.g.: a D-type enriched glufosinate salt (i.e., the content of D-type enantiomer>50%, even pure D-glufosinate salt), an L-type enriched glufosinate salt (i.e., the content of L-glufosinate>50%, excluding pure L-glufosinate salt) or a racemic glufosinate salt, etc.

In the oxidation reaction, the D amino acid oxidase (DAAO) can be in a concentration of conventional in the art, preferably of 0.6-6 U/mL, more preferably of 3.6 U/mL.

In the oxidation reaction, the D-glufosinate salt can be in a concentration of conventional in the art, preferably 100-600 mM, more preferably 300 mM.

The oxidation reaction can also be performed in the presence of catalase.

The oxidation reaction can also be performed under a condition of ventilation. The ventilation is preferably introducing air or oxygen; the rate of the ventilation is preferably 0.5VVM-1VVM. When the oxidation reaction can also be performed under aeration condition, the oxidation reaction can also be performed in the presence of a defoamer.

In the present invention, the air can be the air of conventional in the art, which generally contains oxygen, and the oxygen contained has the content of conventional in the art. It is oxygen in the air that participates in the reaction.

In the oxidation reaction, the reaction system is in a pH of preferably 7-9, more preferably 8. The pH can be achieved by using a buffer. The pH can also be adjusted by using alkali (or alkali solution). The buffer is preferably a phosphate buffer or a Tris-HCl buffer, and the phosphate buffer is preferably a disodium hydrogen phosphate-sodium dihydrogen phosphate buffer or a dipotassium hydrogen phosphate-potassium dihydrogen phosphate buffer. The alkali solution is preferably ammonia water.

In the oxidation reaction, the reaction system can be performed at a conventional temperature in the art, preferably 20-50° C., more preferably 37° C.

The oxidation reaction and the amination reaction can be performed separately or simultaneously (in the same reaction system). The simultaneously means that: in the presence of D-amino acid oxidase (DAAO), L-glutamate dehydrogenase mutant, inorganic amino donor and reduced coenzyme NADPH, a D-glufosinate salt is subjected to an oxidation reaction and an amination reaction to give an L-glufosinate salt.

In the amination reaction, the cation of the L-glufosinate salt can be a cation of conventional in the art, such as an ammonium ion, a sodium ion and/or a potassium ion. It can also be the cation of the buffer used.

In the amination reaction, the cation of the 2-oxo-4-(hydroxymethylphosphinyl) butyrate can be a cation of conventional in the art, such as an ammonium ion, a sodium ion and/or a potassium ions etc. It can also be the cation of the buffer used.

In the amination reaction, the L-glutamate dehydrogenase mutant can be a conventional dosage in the art, for example, 0.09-3 U/ml, preferably 0.3-1.5 U/ml, more preferably 0.9 U/ml.

In the amination reaction, the inorganic amino donor can be a conventional concentration in the art, for example, 100-2000 mM, preferably 600 mM.

In the amination reaction, the 2-oxo-4-(hydroxymethylphosphinyl) butyrate is in a concentration of 100-600 mM, preferably 300 mM.

In the amination reaction, the 2-oxo-4-(hydroxymethylphosphinyl) butyrate can be a conventional dosage in the art, and the molar ratio of the reduced coenzyme NADPH and the 2-oxo-4-(hydroxymethylphosphinyl) butyrate is 1:30000-1:1000, preferably 1:20000-1:5000, more preferably 1:10000.

In the amination reaction, the inorganic amino donor is one or more of ammonia, ammonium sulfate, ammonium chloride, diammonium hydrogen phosphate, ammonium acetate, ammonium formate and ammonium bicarbonate.

In the amination reaction, the reaction can be performed at temperatures conventional in the art. In order to ensure the catalytic efficiency of the L-glutamate dehydrogenase mutant, the amination reaction is performed at a temperature of preferably 20-50° C., more preferably 37° C. When the amination reaction is performed at a temperature of lower than 20° C., the speed of amination reaction is slow; when the amination reaction is performed at a temperature of higher than 50° C., the enzyme will be irreversibly denatured and inactivated.

In the amination reaction, the reaction solvent is water.

In the method, the amination reaction is performed at a pH of preferably 7-9, more preferably 8. The pH can be adjusted by using a buffer. The pH can also be adjusted by using alkali (or alkali solution). The buffer is preferably a phosphate buffer or a Tris-HCl buffer, and the phosphate buffer is preferably a disodium hydrogen phosphate-sodium dihydrogen phosphate buffer or a dipotassium hydrogen phosphate-potassium dihydrogen phosphate buffer. The alkali solution is preferably ammonia water.

The method for preparing the L-glufosinate salt also comprises the following steps: an oxidized coenzyme NADP$^+$ is subjected to a reduction reaction to give the reduced coenzyme NADPH in the presence of dehydrogenase (e.g., glucose dehydrogenase, alcohol dehydrogenase or formate dehydrogenase, etc.) and hydrogen donor (glucose, isopropanol or formate, etc.).

In the reduction reaction, the dehydrogenase has a one-to-one correspondence with the hydrogen donor, for example:

When the dehydrogenase is an alcohol dehydrogenase, the hydrogen donor is an isopropanol;

When the dehydrogenase is a glucose dehydrogenase, the hydrogen donor is a glucose;

When the dehydrogenase is a formate dehydrogenase, the hydrogen donor is a formate.

In the reduction reaction, the dehydrogenase can be of conventional dosage in the art, preferably 0.6-6 U/mL, more preferably 2 U/mL.

In the reduction reaction, the hydrogen donor can be of conventional concentration in the art, preferably 100-1000 mM, more preferably 360 mM.

In the reduction reaction, the oxidized coenzyme NADP$^+$ can be of conventional concentration in the art.

In the reduction reaction, the reduction reaction is performed at a pH of preferably 7-9, more preferably 8. The pH can be adjusted by using a buffer. The pH can also be adjusted by using alkali (or alkali solution). The buffer is preferably a phosphate buffer or a Tris-HCl buffer, etc., and the phosphate buffer is preferably a disodium hydrogen phosphate-sodium dihydrogen phosphate buffer or a dipotassium hydrogen phosphate-potassium dihydrogen phosphate buffer, etc. The alkali solution is preferably ammonia water.

In the reaction system, the reduction reaction can be performed at a temperature of conventional in the art, preferably 20-50° C., more preferably 37° C.

The reduction reaction and the amination reaction can be performed separately or simultaneously (in the same reaction system). The simultaneously, as shown in the preferred embodiment of the present invention, means that: 2-oxo-4-(hydroxymethylphosphinyl) butyrate is subjected to an amination reaction (the reduction reaction of NADP$^+$ exists at the same time) to give an L-glufosinate salt in the presence of glucose dehydrogenase, glucose, oxidized coenzyme NADP$^+$, L-glutamate dehydrogenase mutant and inorganic amino donor.

When the reduction reaction and the amination reaction are performed simultaneously, the NADPH used in the amination reaction can be generated cyclically by the reduction reaction. The oxidized coenzyme NADP$^+$ can be of conventional concentration in the art, preferably 0.02-0.1 mM, more preferably 0.03 mM to ensure that the reaction can be performed normally.

The reduction reaction, the oxidation reaction and the amination reaction can be performed separately or simultaneously (in the same reaction system). The simultaneously, as shown in the preferred embodiment of the present invention, means that: a D-glufosinate salt is subjected to an oxidation reaction and an amination reaction (a reduction reaction of NADP$^+$ exists simultaneously) to give an L-glufosinate salt in the presence of D-amino acid oxidase (DAAO), dehydrogenase, hydrogen donor, oxidized coenzyme NADP$^+$, L-glutamate dehydrogenase mutant and an inorganic amino donor.

When the reduction reaction, the oxidation reaction, and the amination reaction are performed simultaneously, the NADPH used in the amination reaction can be generated cyclically by the reduction reaction. The oxidized coenzyme NADP$^+$ can be of conventional concentration in the art, preferably 0.02-0.1 mM, more preferably 0.03 mM to ensure that the reaction can be performed normally.

The reaction time of the method is as follows: a desired final concentration of the raw materials, or a desired final concentration of products, or a desired conversion rate of products can be achieved under the condition of detection by a conventional method which comprises a pre-column derivatization of high-performance liquid phase chromatography or an ion pair chromatography, etc.

The sixth technical solution that solves the above-mentioned technical problems in the present invention is provided as follows: a preparation method of L-glufosinate, which comprises the following steps:

(1) preparing an L-glufosinate salt according to the above-mentioned method for preparing L-glufosinate salt;

(2) subjecting the L-glufosinate salt prepared in step (1) to an acidification reaction to give an L-glufosinate.

The seventh technical solution that solves the above-mentioned technical problems in the present invention is provided as follows: a use of the L-glutamate dehydrogenase mutant in the preparation of L-glufosinate or salts thereof.

The use in the preparation of L-glufosinate salt can comprises the following steps: 2-oxo-4-(hydroxymethylphosphinyl) butyrate is subjected to an reaction in the presence of an L-amino acid dehydrogenase, an inorganic amino donor and a reduced coenzyme; wherein the L-glutamate dehydrogenase mutant is the L-glutamate dehydrogenase mutant prepared above.

The use in the preparation of L-glufosinate can comprises the following steps: 2-oxo-4-(hydroxymethylphosphinyl) butyric acid is subjected to a reaction to give an L-glufosinate in the presence of an L-amino acid dehydrogenase, an inorganic amino donor and a reduced coenzyme; wherein the L-glutamate dehydrogenase mutant is the L-glutamate dehydrogenase mutant prepared above.

Unless otherwise specified, the concentrations of the above compounds are the concentration of the compound in an entire reaction system before a reaction.

On the basis of conforming to common knowledge in the field, the above-mentioned preferred conditions can be combined arbitrarily to obtain preferred embodiments of the present invention.

The reagents and raw materials used in the present invention are all commercially available.

The positive and progressive effects of the present invention are:

Compared with wild-type L-glutamate dehydrogenase, the L-glutamate dehydrogenase mutant of the present invention can catalyze a higher concentration of substrate when preparing L-glufosinate. In the best embodiment of the related patent CN106978453A, the concentration of the substrate that can be catalysed by 10 mL of L-glutamate dehydrogenase is 10-100 mM, while in the best embodiment of the present invention, the concentration of the substrate that can be catalysed by 15 mL of L-glutamate dehydrogenase mutant has reached 300 mM. The L-glutamate dehydrogenase mutant of the present invention reduces the reaction costs and facilitates industrial production.

DETAILED DESCRIPTION OF THE PREFERRED EMBODIMENT

Figure 1:
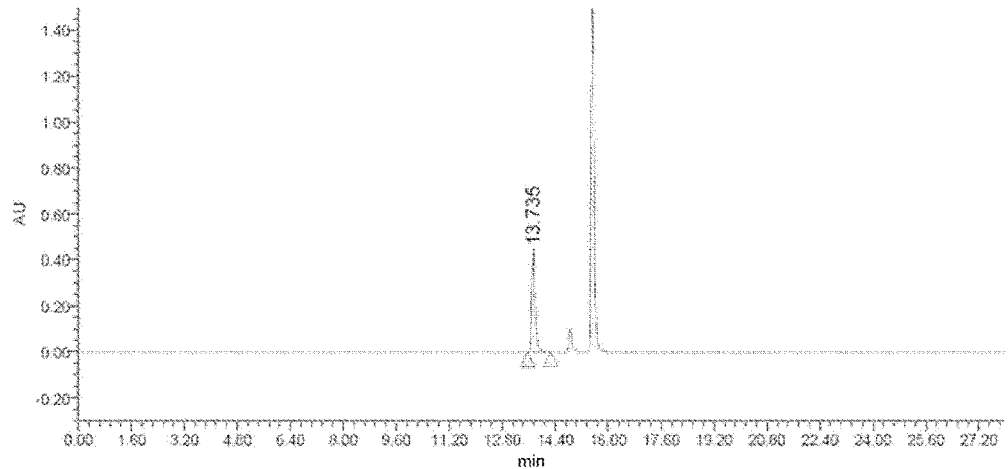
FIG. 1 shows Marfey's reagent pre-column derivatization HPLC analysis result of D-glufosinate and L-glufosinate in the prepared product when L-glutamate dehydrogenase mutant 14 participated in the reaction.

The present invention will be further illustrated by the following examples, but the present invention is not limited to the scope of examples thereto. The experimental methods for which specific conditions are not indicated in the following examples shall be selected according to conventional methods and conditions, or according to the specification of commodity.

Unless otherwise specified, the experimental methods of the present invention are conventional methods, and specific gene cloning operations can be found in the "Molecular Cloning: A Laboratory Manual" compiled by J. Sambrook et al.

Unless otherwise specified, the abbreviations of amino acids in the present invention are conventional in the art, and the amino acids corresponding to the specific abbreviations are shown in Table 1.

TABLE 1

| Name of Amino Acid | Three-Letter Code | Single Letter Code |
|---|---|---|
| alanine | Ala | A |
| arginine | Arg | R |
| asparagine | Asn | N |
| aspartic acid | Asp | D |
| cysteine | Cys | C |
| glutanine | Gln | Q |
| glutamic acid | Glu | E |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |
| tyrosine | Tyr | Y |
| valine | Val | V |

The codons corresponding to the amino acids are also conventional in the art, and the corresponding relationships between specific amino acids and codons are shown in Table 2.

TABLE 2

| First Nucleotide | Second Nucleotide | | | | Third Nucleotide |
|---|---|---|---|---|---|
| | T | C | A | G | |
| T | F(Phenylalanine) | S(Serine) | Y(Tyrosine) | C(Cysteine) | T |
| | F(Phenylalanine) | S(Serine) | Y(Tyrosine) | C(Cysteine) | C |
| | L(Leucine) | S(Serine) | Stop Codon | Stop Codon | A |
| | L(Leucine) | S(Serine) | Stop Codon | W(Tryptophan) | G |
| C | L(Leucine) | P(Proline) | H(Histidine) | R(Arginine) | T |
| | L(Leucine) | P(Proline) | H(Histidine) | R(Arginine) | C |
| | L(Leucine) | P(Proline) | Q(Glutamine) | R(Arginine) | A |
| | L(Leucine) | P(Proline) | Q(Glutamine) | R(Arginine) | G |
| A | I(Isoleucine) | T(Threonine) | N(Asparagine) | S(Serine) | T |
| | I(Isoleucine) | T(Threonine) | N(Asparagine) | S(Serine) | C |
| | I(Isoleucine) | T(Threonine) | K(Lysine) | R(Arginine) | A |
| | M(Methionine) | T(Threonine) | K(Lysine) | R(Arginine) | G |
| G | V(Valine) | A(Alanine) | D(Aspartic acid) | G(Glycine) | T |
| | V(Valine) | A(Alanine) | D(Aspartic acid) | G(Glycine) | C |
| | V(Valine) | A(Alanine) | E(Glutamate) | G(Glycine) | A |
| | V(Valine) | A(Alanine) | E(Glutamate) | G(Glycine) | G | pET28a, pET21a and bugbuster protein extraction reagent were purchased from Novagen; DpnI enzyme was purchased from Invitrogen Shanghai Trading Co., Ltd.; NdeI and HindIII were purchased from Thermo Fisher, and *E. coli* BL21 (DE3) competent cells were purchased From Beijing Dingguo Changsheng Biotechnology Co., Ltd.; the catalase was purchased from Shandong Fengtai Biotechnology Co., Ltd.

The chiral analysis of the product was performed by pre-column derivatization high performance liquid chromatography (HPLC), and the specific analysis method is as follows:

(1) Chromatographic conditions: Agilent ZORBAX Eclipse plus C18, 3.5 μm, 150*4.6 mm. Mobile phase A: 0.1% TFA+$H_2O$, mobile phase B: 0.1% TFA+CAN. Detection wavelength: 340 nm, flow rate: 1.0 mL/min, column temperature: 30° C.

(2) Derivatization reagent: Marfey's reagent. 50 mg of N-α-(2,4-dinitro-5-fluorophenyl)-L-alaninamide was weighed accurately, and dissolved with acetonitrile to prepare 25 ml solution for later use.

(3) Derivatization reaction: The reaction solution was diluted 100 times and added with equal volume of Marfey's reagent for derivatization. 10 μl of mixture was injected for analysis.

Conversion rate=(reactant-remaining reactant)/reactant×100%

2-oxo-4-(hydroxymethylphosphinyl) butyric acid (PPO for short) was analyzed by ion-pair high performance liquid chromatography (HPLC). The specific analysis method is as follows: Chromatographic conditions: Ultimate AQ-C18, 5 μm, 4.6*250 mm; mobile phase: 0.05 mol/L diammonium hydrogen phosphate PH=3.6:10% tetrabutylammonium hydroxide aqueous solution: acetonitrile=91:1:8; detection wavelength: 205 nm; flow rate: 1.0 ml/min; column temperature: 25° C.

Example 1 Construction of L-Glutamate Dehydrogenase Mutant Library

Table 3 shows the sequence of primers designed for the construction of a mutant library with mutations at positions 166, 376, and 196 of SEQ ID NO. 1 in the sequence list.

Wherein, N represents any one of nucleotide A, G, C, T, and M represents A or C, and K represents G or T; the corresponding nucleotide was selected according to the nucleotides encoding the desired amino acid to be mutated at the specific position. For example, NNK in A166-forward primer can represent AAG (lysine), AAT (aspartic acid), AGG (arginine) or AGT (serine), etc. The nucleotides corresponding to specific amino acids can be found in Table 2.

Gene cgGLUDH (*Corynebacterium glutamicum*) was synthesized by Suzhou Genewiz Biotechnology Co., Ltd. (Building C3, Bionano Technology Park, Xinghu Street 218, Suzhou Industrial Park) according to the sequence of SEQ ID NO. 1 in the sequence list, and the PDB number of cgGLUDH is 5IJZ. Then NdeI and HindIII restriction sites were introduced to the plasmid pET21a to construct plasmid pET21a-cgGLUDH. Using the plasmid pET21a-cgGLUDH as a template, the target band was amplified by PCR.

The PCR amplification system is as follows:

| Reagents | Dosage (μL) |
| --- | --- |
| 2 × PCR buffer (contains high fidelity enzyme) | 25 |
| Primer F | 1 |
| Primer R | 1 |
| Template | 1 |
| Deionized Water | 22 |

The PCR amplification procedure is as follows:

| | | |
| --- | --- | --- |
| 95° C. | 5 min | |
| 95° C. | 40 s | |
| 50° C. | 40 s | 30 cycles |
| 72° C. | 6 min | |
| 72° C. | 10 min | |
| 12° C. | heat preservation | |

The PCR product was digested with DpnI at 37° C. for 2 hr. Then the product was transformed into *E. coli* BL21 (DE3) competent cells after the reaction was completed, which were spreaded on LB medium containing 100 μg/mL ampicillin and cultured at 37° C. overnight. The bacteria was harvested, and transformants containing the mutant library were obtained.

TABLE 3

| Mutation Site and No. Primer Name | Primer Sequence | SEQ ID NO. |
| --- | --- | --- |
| 1 A166-forward primer | GAATATCGCGATGTTCCGNNKGGTGATATTGGTGTGGG | 2 |
| 2 A166-reverse primer | CCCACACCAATATCACCMNNCGGAACATCGCGATATTC | 3 |
| 3 V376-forward primer | GCAAATGCCGGCGGTNNKGCGACCAGTGCACTG | 4 |
| 4 V376-reverse primer | CAGTGCACTGGTCGCMNNACCGCCGGCATTTGC | 5 |
| 5 T196-forward primer | GAATCAGGTGTGCTGNNKGGTAAAGGCCTGACC | 6 |
| 6 T196-reverse primer | GGTCAGGCCTTTACCMNNCAGCACACCTGATTC | 7 |

Example 2 High-Throughput Screening of Mutant Libraries

Screening was performed according to the following experimental steps:

The transformants were inoculated and cultured in 96-wells plate and induced with IPTG at 30° C. overnight. The bacteria was harvested, and lysed by bugbuster protein extraction reagent, thus obtaining the enzyme solution by centrifugation.

A reaction solution with final concentrations of 20 mM PPO, 200 mM NH$_4$Cl, and 0.37 mM NAD was prepared. 180 μL of the reaction solution was pipetted to the microplate and then 20 μL of enzyme solution was added to obtain a total system of 200 μL. OD$_{340}$ value was measured by the microplate reader. Taking the wild type as reference system, positive clones were selected, sequenced and the enzyme activity of which was detected. Sequence was conducted by Shenggong Bioengineering (Shanghai) Co., Ltd., No. 698, Xiangmin Road, Songjiang District, Shanghai.

Selected positive clones were cultivated as follows:

The composition of LB liquid medium consists of: peptone 10 g/L, yeast powder 5 g/L, NaCl 10 g/L, after dissolving them in deionized water, make the volume constant, sterilized at 121° C. for 20 min for later use.

A single clone was selected and inoculated into 5 ml LB liquid medium containing 100 μg/ml ampicillin, and cultured with shaking at 37° C. for 12 h. 2% of inoculum was transferred to 50 ml fresh LB liquid medium containing 100 μg/ml ampicillin, shook at 37° C. until OD$_{600}$ value reached about 0.8. IPTG was added to a final concentration of 0.5 mM for induced culturing at 18° C. for 16 h. After cultivation, the culture solution was centrifuged at 10,000 rpm for 10 min, the supernatant was discarded, and the bacteria was collected and stored in an ultra-low temperature refrigerator at −20° C. for later use.

After culturing, the collected bacteria was washed twice with 50 mM phosphate buffer solution, pH 8.0, resuspended in phosphate buffer solution with pH 8.0, and lysed homogeneously at low temperature and high pressure. The lysis liquid was centrifuged to remove cell pellets, thus obtaining supernatant as a crude enzyme solution containing recombinant L-glutamate dehydrogenase mutant.

The detection method of enzyme activity is as follows: 25 g/L wet bacteria (lysed by homogenizer), 10 mM PPO, 20 mM coenzyme (NADPH), 750 mM NH$_4$Cl, with a total system of 400 μL and a pH 8.0 disodium hydrogen phosphate-sodium dihydrogen phosphate buffer as reaction medium. The total system was reacted in a metal bath shaking reactor at 30° C. for 6 h, and the reaction was terminated by adding 2 times of acetonitrile. After the sample was diluted by a certain folds, the concentration of L-glufosinate was detected by pre-column derivatization high performance liquid phase, and the enzyme activity was calculated. The results are shown in Table 4.

The unit of enzyme activity is defined by the amount of enzyme required to produce 1 μmol of L-glufosinate per minute under specific reaction conditions (30° C.).

TABLE 4

| Mutant No. | Mutation Site | Enzyme Acitivity | Amino Acid SEQ ID NO. | Nucleotide SEQ ID NO. |
|---|---|---|---|---|
|  | WT | * | 1 |  |
| 1 | V376A | ** | 8 | 9 |
| 2 | V376G | ** | 10 | 11 |
| 3 | A166G, V376P | ** | 12 | 13 |
| 4 | A166G, V376A | ** | 14 | 15 |
| 5 | A166G, V376S, T196V | ** | 16 | 17 |
| 6 | A166E, V376G | ** | 18 | 19 |
| 7 | A166C, V376A | ** | 20 | 21 |
| 8 | A166G | *** | 22 | 23 |
| 9 | A166G, V376G | *** | 24 | 25 |
| 10 | A166G, V376E | *** | 26 | 27 |
| 11 | A166G, V376Q | *** | 28 | 29 |
| 12 | A166G, V376S, T196S | *** | 30 | 31 |
| 13 | A166T | *** | 32 | 33 |
| 14 | A166G, V376S | **** | 34 | 35 |
| 15 | A166G, V376S, T196C | **** | 36 | 37 |
| 16 | A166H, V376S | **** | 38 | 39 |

Wherein, * means that the enzyme activity is less than 1 U/ml,  means that the enzyme activity is between 3-5 U/ml; * means that the enzyme activity is between 5-10 U/ml; **** means that the enzyme activity is 10 U/ml or more.

Methods for preparing the crude enzyme solution of L-glutamate dehydrogenase used in the following examples are all as described above.

Example 3 Acquisition of D Amino Acid Oxidase (DAAO) Gene

The whole gene of DAAO was synthesized according to the gene sequence of AC302 DAAO described in U.S. Pat. No. 9,834,802B2. Synthesis was conducted by Suzhou Genewiz Biological Technology Co., Ltd., No. 211 Pubin Road, R & D Park, Jiangbei New District, Nanjing, Jiangsu Province.

Example 4 Expression of D Amino Acid Oxidase (DAAO) Gene

The composition of LB liquid medium is as follows: peptone 10 g/L, yeast powder 5 g/L, NaCl 10 g/L, after dissolving them in deionized water and calibrated to a constant volume, LB liquid medium was sterilized at 121° C. for 20 min for later use.

DAAO gene synthesized in Example 3 was ligated to pET28a, with restriction sites NdeI & HindIII, and the ligated vector was transformed into host E. coli BL21 (DE3) competent cells to obtain engineered strains containing DAAO.

After activating the engineered strain containing DAAO gene by streaking on a plate, a single colony was selected and inoculated into 5 ml of LB liquid medium containing 100 μg/ml ampicillin, and cultured with shaking at 37° C. for 12 h. 2% of inoculum was transferred to 50 ml of fresh LB liquid medium containing 100 μg/ml ampicillin, shook at 37° C. until the OD$_{600}$ value reached about 0.8. IPTG was added to a final concentration of 0.5 mM for induced culturing at 18° C. for 16 h. After cultivation, the culture solution was centrifuged at 10,000 rpm for 10 min, the supernatant was discarded, and the bacteria was collected and stored in an ultra-low temperature refrigerator at −20° C. for later use.

Example 5 Preparation of D Amino Acid Oxidase (DAAO) Crude Enzyme Solution and Enzyme Activity Detection After culturing, the collected bacteria in Example 4 was washed twice with 50 mM phosphate buffer solution, pH 8.0, resuspended in phosphate buffer solution with pH 8.0, and lysed homogeneously at low temperature and high pressure. The lysis liquid was centrifuged to remove cell pellets, thus obtaining supernatant as a crude enzyme solution containing recombinant DAAO.

The detection method of enzyme activity is as follows: 100 μL of pH 8.0 disodium hydrogen phosphate-sodium dihydrogen phosphate buffer (containing 50 mmol/L of D-glufosinate and 0.1 mg/mL of peroxidase), 50 μL of indicator (60 μg/mL of 2,4,6-tribromo-3-hydroxybenzoic acid and 1 mg/mL of 4-aminoantipyrine), 50 μL of DAAO enzyme were added, the concentration of $H_2O_2$ was determined by detecting UV absorption at 510 nm, the concentration of PPO was calculated and the enzyme activity was obtained.

The unit of enzyme activity is defined by the amount of enzyme required to produce 1 μmol of PPO per minute under specific reaction conditions (30° C.).

Methods for preparing the crude enzyme solution of DAAO enzyme used in the following examples are all as described above.

Example 6 Acquisition and Expression of Glucose Dehydrogenase Gene

The whole gene of glucose dehydrogenase was synthesized according to the glucose dehydrogenase gene sequence from *Bacillus subtilis* 168 (NCBI accession number: NP 388275.1).

The composition of LB liquid medium consists of: peptone 10 g/L, yeast powder 5 g/L, NaCl 10 g/L, after dissolving them in deionized water, make the volume constant, and sterilized at 121° C. for 20 min for later use.

Glucose dehydrogenase gene was ligated to pET28a, with restriction sites NdeI & HindIII, and the ligated vector was transformed into host *E. coli* BL21 (DE3) competent cells to obtain engineered strains containing glucose dehydrogenase gene. After activating the engineered strains containing glucose dehydrogenase gene by streaking them on a plate, a single colony was selected and inoculated into 5 ml of LB liquid medium containing 100 μg/ml ampicillin, and cultured with shaking at 37° C. for 12 h. 2% of inoculum was transferred to 50 ml of fresh LB liquid medium containing 100 μg/ml ampicillin, shook at 37° C. until the $OD_{600}$ value reached about 0.8. IPTG was added to a final concentration of 0.5 mM for induced culturing at 18° C. for 16 h. After cultivation, the culture solution was centrifuged at 10,000 rpm for 10 min, the supernatant was discarded, and the bacteria was collected and stored in an ultra-low temperature refrigerator at −20° C. for later use.

Example 7 Preparation of Crude Glucose Dehydrogenase Solution and Detection of Enzyme Activity After culturing, the collected bacteria in Example 6 was washed twice with 50 mM pH 8.0 phosphate buffer solution, resuspended in pH 8.0 phosphate buffer solution, and lysed homogeneously at low temperature and high pressure. The lysis liquid was centrifuged to remove cell pellets, thus obtaining supernatant as a crude enzyme solution containing recombinant glucose dehydrogenase.

The detection method of enzyme activity is as follows: in 1 mL reaction system and under the condition of 25° C., first, 980 μL of 50 mM of sodium hydrogen phosphate-sodium dihydrogen phosphate buffer (containing 400 mM glucose) with pH 7.0 was added, then 10 μL of NADP+ (25 mM) was added, and finally 10 μL of appropriate enzyme solution was added, thus measuring OD value at 340 nm by an ultraviolet spectrophotometer.

The unit of enzyme activity is defined by the amount of enzyme required to produce 1 μmol of NADPH per minute under specific reaction conditions (30° C.).

Methods for preparing the crude enzyme solution of glucose dehydrogenase used in the following examples are all as described above.

Example 8 Preparation of Crude Alcohol Dehydrogenase Solution and Enzyme Activity Test The whole gene of alcohol dehydrogenase was synthesized according to the Cyclopentanol dehydrogenase gene sequence from *Lactobacillus brevis* KB290 (Genbank accession number: BAN05992.1).

Alcohol dehydrogenase gene was ligated to pET28a, with restriction sites NdeI & HindIII, and the ligated vector was transformed into host *E. coli* BL21 (DE3) competent cells to obtain engineered strains containing glucose dehydrogenase gene. After activating the engineered strains containing glucose dehydrogenase gene by streaking them on a plate, a single colony was selected and inoculated into 5 ml of LB liquid medium containing 100m/m1 ampicillin, and cultured with shaking at 37° C. for 12 h. 2% of inoculum was transferred to 50 ml of fresh LB liquid medium containing 100m/m1 ampicillin, shook at 37° C. until the $OD_{600}$ value reached about 0.8. IPTG was added to a final concentration of 0.5 mM for induced culturing at 18° C. for 16 h. After cultivation, the culture solution was centrifuged at 10,000 rpm for 10 min, the supernatant was discarded, and the bacteria was collected and stored in an ultra-low temperature refrigerator at −20° C. for later use.

50 ml of 100 mM pH7.5 ammonium phosphate buffer was added to 10 g of bacteria mud, stirred well, and lysed homogenously at 500 bar to obtain a crude enzyme solution. 10% of flocculant was added dropwise under stirring conditions (in a final concentration of 2-2.5%0). After stirring for 5 minutes, the solution was centrifuged at 4,000 rpm for 10 minutes to obtain a clear enzyme solution. The supernatant was took to detect enzyme activity.

The method for detecting enzyme activity is as follows: in a 3 mL of reaction system and under the condition of 25° C., first, a 2850 μL of 400 mM isopropanol (prepared with 100 mM phosphate buffer) with pH 8.0 was added first, then 50 μL of NADP+ (25 mM) was added. After adjusting the UV spectrophotometry meter to zero, then 100 μL of enzyme solution diluted 100 folds was added, and OD value at 340 nm was measured by an ultraviolet spectrophotometer.

The unit of enzyme activity is defined as follows: the amount of enzyme required to produce 1 μmol of NADPH per minute under specific reaction conditions (25° C., pH 8.0) is defined as 1 U.

Methods for preparing the crude enzyme solution of alcohol dehydrogenase used in the following examples are all as described above.

Example 9 Preparation of L-Glufosinate Catalysed by L-Glutamate Dehydrogenase Mutant PPO, NADP+, $NH_4Cl$ and glucose were weighed and added to the reaction flask, and dissolved completely with 50 mM of disodium hydrogen phosphate-sodium dihydrogen phosphate buffer with pH 8.0. The pH was adjusted to 8.0 with 25% concentrated ammonia water. 15 mL of the crude enzyme solution of L-glutamate dehydrogenase mutants 1(1

U/mL), 2 (1.3 U/mL), 8 (2.1 U/mL), 14 (3 U/mL), 15 (2.8 U)/mL) and 16 (2.5 U/mL) prepared according to the method in Example 2, and 1 mL of the crude enzyme solution of glucose dehydrogenase (100 U/mL) prepared according to the method in Example 7 were added, 50 mM of disodium hydrogen phosphate-sodium dihydrogen phosphate buffer with pH 8.0 was used to make the volume constant to 50 mL, so that the final concentration of PPO, ammonium chloride, glucose and NADP$^+$ were 300 mM 600 mM, 360 mM and 0.03 mM, respectively. During the reaction process, the pH was controlled at 8.0 with ammonia water, and the residual concentration of PPO was measured by ion-pair HPLC after reacting in water bath using magnetic stirring for 10 h at 37° C. Meanwhile the production and ee value of L-glufosinate were determined by pre-column derivatization high performance liquid chromatography.

The data at the end of the reaction are shown in Table 5. In the best embodiment of CN106978453A, the substrate that can be catalysed by 10 mL of L-glutamate dehydrogenase is in the concentration of 10-100 mM, while the substrate that can be catalysed by 15 mL of L-glutamate dehydrogenase mutant has reached a concentration of 300 mM in the present example.

Figure 2:
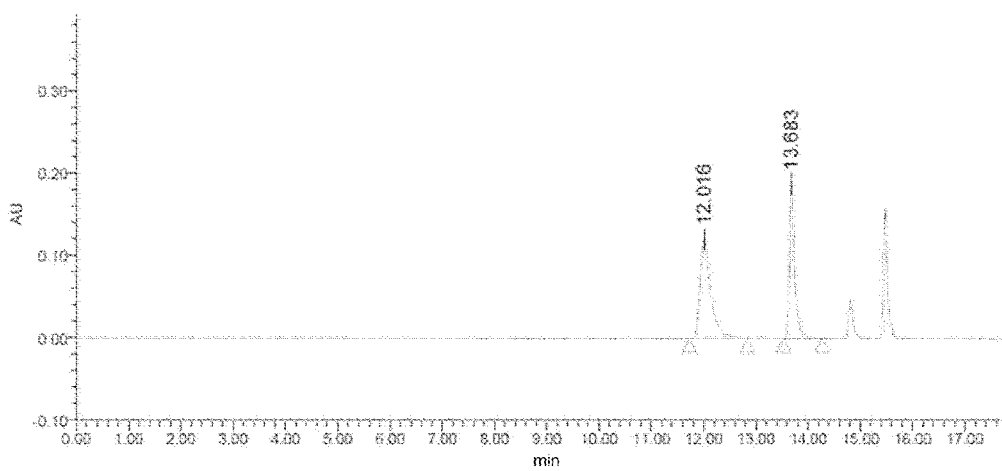
FIG. 2 shows Marfey's reagent pre-column derivatization HPLC analysis result of racemic glufosinate standard, wherein the last two peaks are the peaks of the Marfey's reagent blank sample.

The HPLC analysis results of D-glufosinate and L-glufosinate in the products are shown in FIG. 1 (in the drawings, L-glutamate dehydrogenase mutant 14 is used as an example for illustration), wherein the retention time of the L-glufosinate is 13.735 min, and D-glufosinate is almost undetectable; the HPLC chromatogram of Marfey's reagent pre-column derivatization of the racemic glufosinate standard (purchased from Shanghai Aladdin Biochemical Technology Co., Ltd.) is shown in FIG. 2 (the retention time of L-glufosinate and D-glufosinate are 13.683 min and 12.016 min, respectively). The peak time of the composition of the product prepared in this example is generally the same with that of the L-glufosinate in the standard product, indicating that L-glufosinate was prepared in present example.

Figure 3:
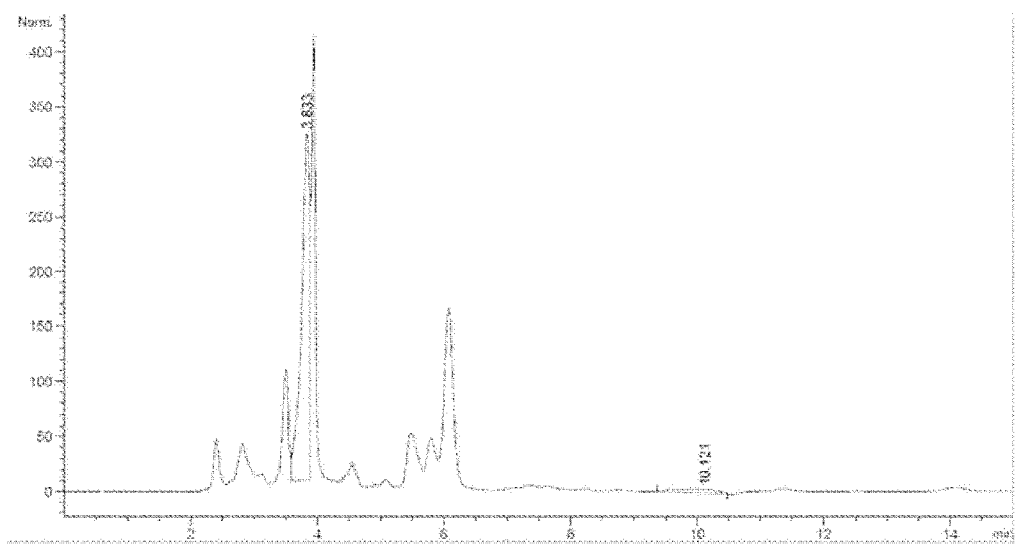
FIG. 3 shows ion-pair HPLC analysis result of L-glufosinate prepared when L-glutamate dehydrogenase mutant 14 participated in the reaction.
Figure 4:
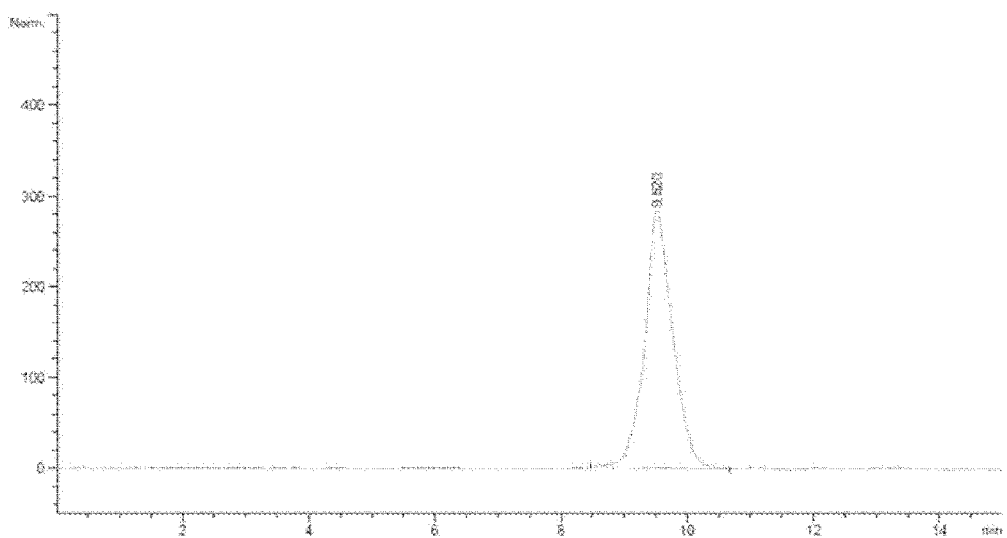
FIG. 4 shows ion pair HPLC analysis result of PPO standard.
Figure 5:
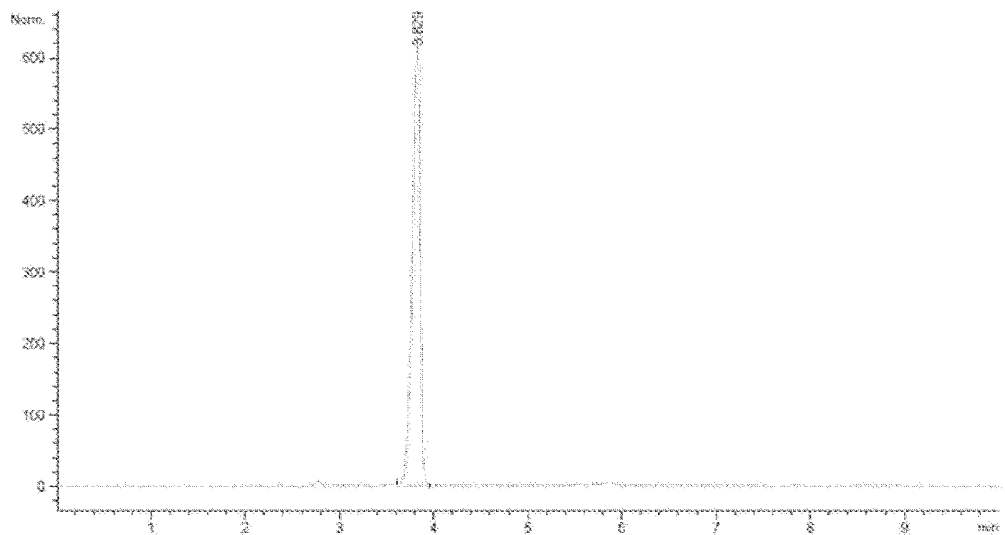
FIG. 5 shows ion-pair HPLC analysis result of racemic glufosinate standard.
Figure 6:
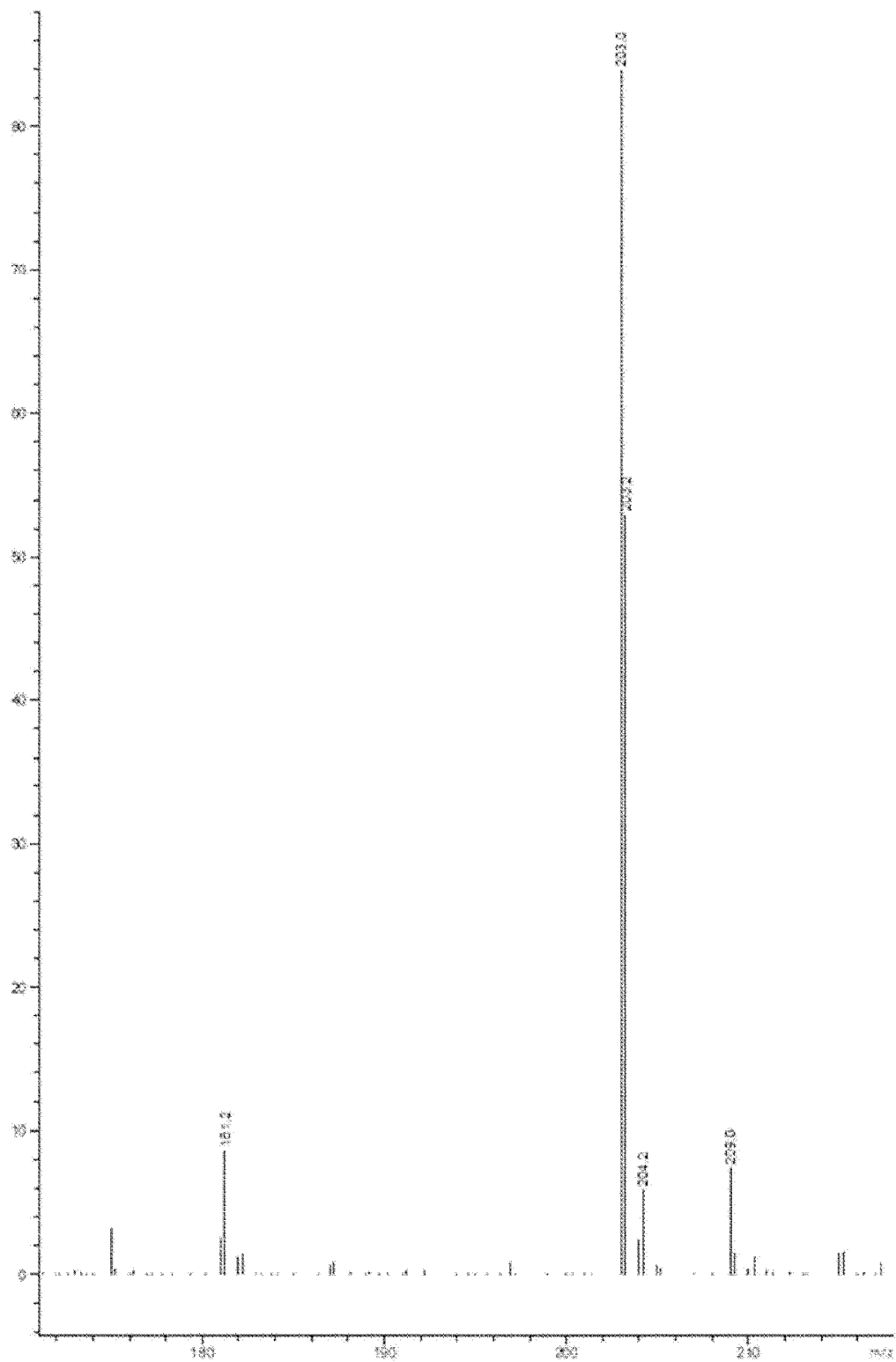
FIG. 6 shows mass spectrum of PPO standard.

The ion-pair HPLC analysis results of the prepared PPO are shown in FIG. 3. Wherein, 10.121 min is the peak position of PPO, and 3.833 min is the peak position of L-glufosinate. The ion pair HPLC spectrum of the PPO standard product (this standard product is made by the laboratory self, and the method for preparing was referred to U.S. Pat. No. 8,017,797B, FIG. 6 is the corresponding mass spectrum) is shown in FIG. 4, wherein the retention time of PPO standard product is 9.520 min. The ion pair HPLC spectrum of the racemic glufosinate standard (purchased from Shanghai Aladdin Biochemical Technology Co., Ltd.) is shown in FIG. 5, wherein the retention time of racemic glufosinate standard is 3.829 min. It shows that the peak time of PPO and product glufosinate in this example are generally consistent with the peak time of their respective standards.

Although L-glutamate dehydrogenase mutant 14 is taken as an example in the above results, experiments on all other mutations were conducted by inventors to verify that the substrate can by catalyzed by these mutations of the present invention when participating in above reaction, thereby producing correct products.

TABLE 5

| Enzyme No. of Mutant | PPO conversion rate | ee value |
| --- | --- | --- |
| 1 | 10% | 90% |
| 2 | 15% | 92% |

TABLE 5-continued

| Enzyme No. of Mutant | PPO conversion rate | ee value |
| --- | --- | --- |
| 8 | 45% | 95% |
| 14 | 99% | >99% |
| 15 | 98% | >99% |
| 16 | 97% | >99% |

Example 10 Preparation of L-Glufosinate Catalyzed by DAAO and L-glutamate Dehydrogenase Mutants D, L-glufosinate, NADP$^+$, NH$_4$Cl and glucose were weighed and added to the reaction flask, and dissolved completely with 50 mM of disodium hydrogen phosphate-sodium dihydrogen phosphate buffer, pH 8.0. The pH was adjusted to 8.0 with 25% concentrated ammonia water. 15 mL of crude enzyme solution of DAAO enzyme (12 U/mL) prepared according to the method in Example 5, 0.2 g of 200,000 U/g catalase, 15 mL of crude enzyme solution of L-glutamate dehydrogenase mutant 1 (1 U/mL) prepared according to Example 2 or L-glutamate dehydrogenase mutant 14 (3 U/mL), and 1 mL of crude enzyme solution of glucose dehydrogenase (100 U/mL) prepared according to the method in Example 7 were added, and 50 mM of disodium hydrogen phosphate-sodium dihydrogen phosphate buffer, pH 8.0, was used to make the volume constant to 50 mL, so that the concentration of glufosinate, ammonium chloride, glucose and NADP$^+$ were 600 mM, 600 mM, 360 mM and 0.03 mM, respectively. During the reaction process, the pH was controlled at 8.0 with ammonia water, and magnetic stirring was carried out in a water bath at 37° C. Air was ventilated at 1 VVM (ventilate 1 times the reaction volume of air per minute), 200 µL of defoamer was added to prevent foaming, and the residual concentration of PPO was determined by ion-pair HPLC after reaction for 24 h, thereby determining the production mass and ee value of L-glufosinate by pre-column derivatization high performance liquid chromatography simultaneously. The data at the end of the reaction is shown in Table 6.

TABLE 6

| Enzyme No. of Mutant | PPO conversion rate | ee value |
| --- | --- | --- |
| 1 | 90% | 90% |
| 14 | 99% | >99% |

Example 11 Preparation of L-Glufosinate Catalysed Stepwise by DAAO and L-Glutamate Dehydrogenase Mutants 80 g of D, L-glufosinate was weighed, and dissolved completely with 50 mM of disodium hydrogen phosphate-sodium dihydrogen phosphate buffer, pH 8.0. 5 g of 200,000 U/g catalase was added, 150 mL of crude enzyme solution of DAAO enzyme (12 U/mL) prepared according to the method in Example 5 was added, and the pH was adjusted to 8.0 with 25% concentrated ammonia water. 50 mM of disodium hydrogen phosphate-sodium dihydrogen phosphate buffer, pH 8.0, was used to make the volume constant to 1 L. The reaction was performed in a water bath at 20° C. and mechanically stirred, and oxygen was ventilated at 0.5 VVM (ventilate 0.5 times the reaction volume of oxygen per minute). 1 mL of defoamer was added to prevent foaming, the production concentration of PPO was determined by ion-pair HPLC, and the production mass and ee value of L-glufosinate were determined with pre-column derivatization high performance liquid chromatography simultaneously. The reaction was terminated when the ee value was greater than 99%.

2 aliquots of 50 mL of the above reaction solutions were added with 0.54 g of ammonium chloride, 0.4 mg of NADP$^+$ and 0.73 g of isopropanol, respectively. 1 mL of alcohol dehydrogenase (300 U/mL) prepared according to the method in Example 8 and 1 mL of crude enzyme solution of L-glutamate dehydrogenase mutant were added, respectively. The pH was adjust to 8.5 with ammonia water, and the reaction temperature was controlled by performing reaction in water bath and magnetically stirred at 37° C. The residual concentration of PPO was determined by ion-pair HPLC, and the production mass and ee value of L-glufosinate were determined by pre-column derivatization high performance liquid chromatography simultaneously. The data at the end of the reaction is shown in Table 7.

TABLE 7

| Enzyme No. of Mutant | PPO conversion rate | ee value |
| --- | --- | --- |
| 1 | 92% | 90% |
| 14 | 99% | >99% |

Although specific embodiments of the present invention have been described above, it shall be understood by those skilled in the art that the foregoing description of embodiments is intended to be purely illustrative of the invention, and various changes or modifications can be made without departing from the principle and essence of the present invention. Therefore, the scope of protection of the present invention is defined by the appended claims.

What is claimed is:

1. An L-glutamate dehydrogenase mutant, wherein the amino acid sequence of the L-glutamate dehydrogenase mutant is SEQ ID NO: 34.

2. A method for producing an L-glufosinate salt, wherein the method comprises the following step: combining the L-glutamate dehydrogenase mutant of claim 1, 2-oxo-4-(hydroxymethylphosphinyl) butyrate, an inorganic amino donor, and NADPH in a reaction solvent to produce the L-glufosinate salt.

3. The method of claim 2, wherein the method further comprises the following step: combining a D-glufosinate salt with a D-amino acid oxidase to produce the 2-oxo-4-(hydroxymethylphosphinyl) butyrate.

4. The method of claim 2, wherein the method comprises one or more of the following conditions:
the L-glutamate dehydrogenase mutant has a concentration of 0.09-3 U/ml;
the inorganic amino donor has a concentration of 100-2000 mM;
the 2-oxo-4-(hydroxymethylphosphinyl) butyrate has a concentration of 100-600 mM;
the molar ratio of NADPH to the 2-oxo-4-(hydroxymethylphosphinyl) butyrate is 1:30000-1:1000;
the inorganic amino donor is one or more of ammonia, ammonium sulfate, ammonium chloride, diammonium hydrogen phosphate, ammonium acetate, ammonium formate, and ammonium bicarbonate;
the reaction solvent is water;
a pH of 7-9; and
a temperature of 20-50° C.

5. The method of claim 2, wherein the method further comprises the following step: the NADPH is oxidized to $NADP^-$ and the $NADP^-$ is reduced to NADPH by a dehydrogenase and a hydrogen donor.

6. The method of claim 5, wherein the method comprises one or more of the following conditions:
the dehydrogenase that reduces $NADP^-$ to NADPH has a concentration of 0.6-6 U/mL;
the $NADP^-$ has a concentration of 0.02-0.1 mM;

the hydrogen donor has a concentration of 100-1000 mM;
a pH of 7-9; and
a temperature of 20-50° C.

7. An isolated nucleic acid comprising a nucleotide sequence encoding the L-glutamate dehydrogenase mutant of claim 1.

8. The method of claim 3, wherein the method comprises one or more of the following conditions:
the D-glufosinate salt is purified or is mixed with an L-glufosinate salt;
the D-amino acid oxidase has a concentration of 0.6-6 U/mL;
the combining is performed in the presence of oxygen;
the combining is performed in the presence of catalase;
the D-glufosinate salt has a concentration of 100-600 mM;
a pH of 7-9; and
a temperature of 20-50° C.

9. The method of claim 5, wherein the dehydrogenase that reduces $NADP^-$ to NADPH is a glucose dehydrogenase, an alcohol dehydrogenase or a formate dehydrogenase; and/or, the hydrogen donor is glucose, isopropanol or formate.

\* \* \* \* \*

SEQUENCE LISTING

<160> NUMBER OF SEQ ID NOS: 39

<210> SEQ ID NO 1
<211> LENGTH: 447
<212> TYPE: PRT
<213> ORGANISM: Corynebacterium glutamicum

<400> SEQUENCE: 1

```
Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Ala Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
    210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
```

```
                    245                 250                 255
Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
    290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
            325                 330                 335

Asn Gly Cys Arg Phe Val Ala Glu Gly Ala Asn Met Pro Ser Thr Pro
        340                 345                 350

Glu Ala Val Glu Val Phe Arg Glu Arg Asp Ile Arg Phe Gly Pro Gly
    355                 360                 365

Lys Ala Ala Asn Ala Gly Gly Val Ala Thr Ser Ala Leu Glu Met Gln
370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
            405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
        435                 440                 445

<210> SEQ ID NO 2
<211> LENGTH: 38
<212> TYPE: DNA
<213> ORGANISM: Artificial Sequence
<220> FEATURE:
<223> OTHER INFORMATION: A166-forward primer
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: k is g or t

<400> SEQUENCE: 2
gaatatcgcg atgttccgnn kggtgatatt ggtgtggg                          38

<210> SEQ ID NO 3
<211> LENGTH: 38
<212> TYPE: DNA
<213> ORGANISM: Artificial Sequence
<220> FEATURE:
<223> OTHER INFORMATION: A166-reverse primer
<220> FEATURE:
<221> NAME/KEY: misc_feature
<222> LOCATION: (18)..(18)
<223> OTHER INFORMATION: m is a or c
<220> FEATURE:
<221> NAME/KEY: misc_feature
<222> LOCATION: (19)..(20)
<223> OTHER INFORMATION: n is a, c, g, or t

<400> SEQUENCE: 3
cccacaccaa tatcaccmnn cggaacatcg cgatattc                          38
```

```
<210> SEQ ID NO 4
<211> LENGTH: 33
<212> TYPE: DNA
<213> ORGANISM: Artificial Sequence
<220> FEATURE:
<223> OTHER INFORMATION: V376-forward primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: k is g or t

<400> SEQUENCE: 4
gcaaatgccg gcggtnnkgc gaccagtgca ctg                              33

<210> SEQ ID NO 5
<211> LENGTH: 33
<212> TYPE: DNA
<213> ORGANISM: Artificial Sequence
<220> FEATURE:
<223> OTHER INFORMATION: V376-reverse primer
<220> FEATURE:
<221> NAME/KEY: misc_feature
<222> LOCATION: (16)..(16)
<223> OTHER INFORMATION: m is a or c
<220> FEATURE:
<221> NAME/KEY: misc_feature
<222> LOCATION: (17)..(18)
<223> OTHER INFORMATION: n is a, c, g, or t

<400> SEQUENCE: 5
cagtgcactg gtcgcmnnac cgccggcatt tgc                              33

<210> SEQ ID NO 6
<211> LENGTH: 33
<212> TYPE: DNA
<213> ORGANISM: Artificial Sequence
<220> FEATURE:
<223> OTHER INFORMATION: T196-forward primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: k is g or t

<400> SEQUENCE: 6
gaatcaggtg tgctgnnkgg taaaggcctg acc                              33

<210> SEQ ID NO 7
<211> LENGTH: 33
<212> TYPE: DNA
<213> ORGANISM: Artificial Sequence
<220> FEATURE:
<223> OTHER INFORMATION: T196-reverse primer
<220> FEATURE:
<221> NAME/KEY: misc_feature
<222> LOCATION: (16)..(16)
<223> OTHER INFORMATION: m is a or c
<220> FEATURE:
<221> NAME/KEY: misc_feature
<222> LOCATION: (17)..(18)
<223> OTHER INFORMATION: n is a, c, g, or t

<400> SEQUENCE: 7
ggtcaggcct ttaccmnnca gcacacctga ttc                              33
```

<210> SEQ ID NO 8
<211> LENGTH: 447
<212> TYPE: PRT
<213> ORGANISM: Artificial Sequence
<220> FEATURE:
<223> OTHER INFORMATION: L-glutamate dehydrogenase mutant 1 (V376A)

<400> SEQUENCE: 8

```
Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Ala Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
    210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
    290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
        355                 360                 365
```

-continued

```
Lys Ala Ala Asn Ala Gly Gly Ala Ala Thr Ser Ala Leu Glu Met Gln
            370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
        435                 440                 445

<210> SEQ ID NO 9
<211> LENGTH: 1341
<212> TYPE: DNA
<213> ORGANISM: Artificial Sequence
<220> FEATURE:
<223> OTHER INFORMATION: L-glutamate dehydrogenase mutant 1 (V376A)

<400> SEQUENCE: 9
atgaccgttg acgaacaggt ttctaactac tacgacatgc tgctgaaacg taacgctggt     60
gaaccggaat ccaccaggc tgttgctgaa gttctggaat ctctgaaaat cgttctggaa    120
aaagacccgc actacgctga ctacggtctg atccagcgtc tgtgcgaacc ggaacgtcag    180
ctgatcttcc gtgttccgtg ggttgacgac cagggtcagg ttcacgttaa ccgtggtttc    240
cgtgttcagt tcaactctgc tctgggtccg tacaaaggtg gtctgcgttt ccaccgtctg    300
gttaacctgg gtatcgttaa attcctgggt ttcgaacaga tcttcaaaaa ctctctgacc    360
ggtctgccga tcggtggtgg taaaggtggt tctgacttcg acccgaaagg taaatctgac    420
ctggaaatca tgcgtttctg ccagtctttc atgaccgaac tgcaccgtca catcggtgaa    480
taccgtgacg ttccggctgg tgacatcggt gttggtggtc gtgaaatcgg ttacctgttc    540
ggtcactacc gtcgtatggc taaccagcac gaatctggtg ttctgaccgg taaaggtctg    600
acctggggtg ttctctctgt tcgtaccgaa gctaccggtt acggttgcgt ttacttcgtt    660
tctgaaatga tcaaagctaa aggtgaatct atctctggtc agaaaatcat cgtttctggt    720
tctggtaacg ttgctaccta cgctatcgaa aaagctcagg aactgggtgc taccgttatc    780
ggtttctctg actcttctgg ttgggttcac accccgaacg tgttgacgt tgctaaactg    840 cgtgaaatca agaagttcg tcgtgctcgt gtttctgttt acgctgacga agttaaggt    900 gctacctacc acaccgacgg ttctatctgg gacctgaaat gcgacatcgc tctgccgtgc    960
gctacccaga cgaactgaa cggtgaaaac gctaaaccc tggctgacaa cggttgccgt   1020
ttcgttgctg aaggtgctaa catgccgtct accccggaag ctgttgaagt tttccgtgaa   1080
cgtgacatcc gttccggtcc gggtaaagct gctaacgctg tggtgctgc tacctctgct   1140 ctggaaatgc agcagaacgc ttctcgtgac tcttggtctt tcgaatacac cgacgaacgt   1200
ctgcaggtta tcatgaaaaa catcttcaaa acctgcgctg aaaccgctgc tgaatacggt   1260
cacgaaaacg actacgttgt tggtgctaac atcgctggtt tcaaaaaagt tgctgacgct   1320
atgctggctc agggtgttat c                                             1341

<210> SEQ ID NO 10
<211> LENGTH: 447
<212> TYPE: PRT
<213> ORGANISM: Artificial Sequence
<220> FEATURE:
<223> OTHER INFORMATION: L-glutamate dehydrogenase mutant 2 (V376G)
```

<400> SEQUENCE: 10

```
Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Ala Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
    290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
        355                 360                 365

Lys Ala Ala Asn Ala Gly Gly Gly Ala Thr Ser Ala Leu Glu Met Gln
    370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415
```

Ala Glu Tyr Gly His Glu Asn Asp Tyr Val Val Gly Ala Asn Ile Ala
                420                 425                 430

Gly Phe Lys Lys Val Ala Asp Ala Met Leu Ala Gln Gly Val Ile
        435                 440                 445

<210> SEQ ID NO 11
<211> LENGTH: 1341
<212> TYPE: DNA
<213> ORGANISM: Artificial Sequence
<220> FEATURE:
<223> OTHER INFORMATION: L-glutamate dehydrogenase mutant 2 (V376G)

<400> SEQUENCE: 11

| | |
|---|---|
| atgaccgttg acgaacaggt ttctaactac tacgacatgc tgctgaaacg taacgctggt | 60 |
| gaaccggaat tccaccaggc tgttgctgaa gttctggaat ctctgaaaat cgttctggaa | 120 |
| aaagacccgc actacgctga ctacggtctg atccagcgtc tgtgcgaacc ggaacgtcag | 180 |
| ctgatcttcc gtgttccgtg ggttgacgac cagggtcagg ttcacgttaa ccgtggtttc | 240 |
| cgtgttcagt tcaactctgc tctgggtccg tacaaggtg tctgcgtttt ccacccgtct | 300 |
| gttaacctgg gtatcgttaa attcctgggt ttcgaacaga tcttcaaaaa ctctctgacc | 360 |
| ggtctgccga tcggtggtgg taaaggtggt tctgacttcg acccgaaagg taaatctgac | 420 |
| ctggaaatca tgcgttctct ccagtctttc atgaccgaac tgcaccgtca catcggtgaa | 480 |
| taccgtgacg ttccggctgg tgacatcggt gttggtggtc gtgaaatcgg ttacctgttc | 540 |
| ggtcactacc gtcgtatggc taaccagcac gaatctggtg ttctgaccgg taaggtctg | 600 |
| acctggggtg ttctctggt tcgtaccgaa gctaccggtt acggttgcgt ttacttcgtt | 660 |
| tctgaaatga tcaaagctaa aggtgaatct atctctggtc agaaaatcat cgttctggt | 720 |
| tctggtaacg ttgctaccta cgctatcgaa aaagctcagg aactgggtgc taccgttatc | 780 |
| ggtttctctg actcttctgg ttgggttcac accccgaacg tgttgacgt tgctaaactg | 840 |
| cgtgaaatca agaagttcg tcgtgctcgt gtttctgttt acgctgacga agttgaaggt | 900 |
| gctacctacc acaccgacgg ttctatctg gacctgaaat gcgacatcgc tctgccgtgc | 960 |
| gctacccaga cgaactgaa cggtgaaaac gctaaaaccc tggctgacaa cggttgccgt | 1020 |
| ttcgttgctg aaggtgctaa catgccgtct accccggaag ctgttgaagt tttccgtgaa | 1080 |
| cgtgacatcc gtttcggtcc gggtaaagct gctaacgctg tggtggtgc tacctctgct | 1140 |
| ctggaaatgc agcagaacgc ttctcgtgac tcttggtctt cgaatacac cgacgaacgt | 1200 |
| ctgcaggtta tcatgaaaaa catcttcaaa acctgcgctg aaaccgctgc tgaatacggt | 1260 |
| cacgaaaacg actacgttgt tggtgctaac atcgctggtt tcaaaaagt tgctgacgct | 1320 |
| atgctggctc agggtgttat c | 1341 |

<210> SEQ ID NO 12
<211> LENGTH: 447
<212> TYPE: PRT
<213> ORGANISM: Artificial Sequence
<220> FEATURE:
<223> OTHER INFORMATION: L-glutamate dehydrogenase mutant 3 (A166G,
      V376P)

<400> SEQUENCE: 12

Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

```
Glu Ser Leu Lys Ile Val Leu Glu Lys Asp Pro His Tyr Ala Asp Tyr
         35                  40                  45

Gly Leu Ile Gln Arg Leu Cys Glu Pro Glu Arg Gln Leu Ile Phe Arg
 50                  55                  60

Val Pro Trp Val Asp Asp Gln Gly Gln Val His Val Asn Arg Gly Phe
 65                  70                  75                  80

Arg Val Gln Phe Asn Ser Ala Leu Gly Pro Tyr Lys Gly Gly Leu Arg
                 85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
            115                 120                 125

Gly Gly Ser Asp Phe Asp Pro Lys Gly Lys Ser Asp Leu Glu Ile Met
130                 135                 140

Arg Phe Cys Gln Ser Phe Met Thr Glu Leu His Arg His Ile Gly Glu
145                 150                 155                 160

Tyr Arg Asp Val Pro Gly Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
            195                 200                 205

Thr Glu Ala Thr Gly Tyr Gly Cys Val Tyr Phe Val Ser Glu Met Ile
210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
            275                 280                 285

Ala Arg Val Ser Val Tyr Ala Asp Glu Val Glu Gly Ala Thr Tyr His
290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
            355                 360                 365

Lys Ala Ala Asn Ala Gly Gly Pro Ala Thr Ser Ala Leu Glu Met Gln
370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
            435                 440                 445
```

<210> SEQ ID NO 13
<211> LENGTH: 1341
<212> TYPE: DNA
<213> ORGANISM: Artificial Sequence
<220> FEATURE:
<223> OTHER INFORMATION: L-glutamate dehydrogenase mutant 3 (A166G, V376P)

<400> SEQUENCE: 13

```
atgaccgttg acgaacaggt ttctaactac tacgacatgc tgctgaaacg taacgctggt      60
gaaccggaat ccaccaggc tgttgctgaa gttctggaat ctctgaaaat cgttctggaa     120
aaagacccgc actacgctga ctacggtctg atccagcgtc tgtgcgaacc ggaacgtcag     180
ctgatcttcc gtgttccgtg ggttgacgac cagggtcagg ttcacgttaa ccgtggtttc     240
cgtgttcagt tcaactctgc tctgggtccg tacaaaggtg tctgcgtttt ccacccgtct     300
gttaacctgg gtatcgttaa attcctgggt ttcgaacaga tcttcaaaaa ctctctgacc     360
ggtctgccga cggtggtgg taaaggtggt tctgacttcg acccgaaagg taaatctgac     420
ctggaaatca tgcgtttctg ccagtctttc atgaccgaac tgcaccgtca catcggtgaa     480
taccgtgacg ttccgggtgg tgacatcggt gttggtggtc gtgaaatcgg ttacctgttc     540
ggtcactacc gtcgtatggc taaccagcac gaatctggtg ttctgaccgg taaaggtctg     600
acctggggtg ttctctctggt tcgtaccgaa gctaccggtt acggttgcgt ttacttcgtt     660
tctgaaatga tcaaagctaa aggtgaatct atctctggtc agaaaatcat cgtttctggt     720
tctggtaacg ttgctaccta cgctatcgaa aaagctcagg aactgggtgc taccgttatc     780
ggtttctctg actcttctgg ttgggttcac accccgaacg tgttgacgt tgctaaactg     840
cgtgaaatca agaagttcg tcgtgctcgt gtttctgttt acgctgacga agttgaaggt     900
gctacctacc acaccgacgg ttctatctgg gacctgaaat cgacatcgc tctgccgtgc     960
gctacccaga cgaactgaa cggtgaaaac gctaaaaccc tggctgacaa cggttgccgt    1020
ttcgttgctg aaggtgctaa catgccgtct accccggaag ctgttgaagt tttccgtgaa    1080
cgtgacatcc gtttcggtcc gggtaaagct gctaacgctg tggtccggc tacctctgct    1140
ctggaaatgc agcagaacgc ttctcgtgac tcttggtctt cgaatacac cgacgaacgt    1200
ctgcaggtta tcatgaaaaa catcttcaaa acctgcgctg aaaccgctgc tgaatacggt    1260
cacgaaaacg actacgttgt tggtgctaac atcgctggtt tcaaaaaagt tgctgacgct    1320
atgctggctc agggtgttat c                                              1341
```

<210> SEQ ID NO 14
<211> LENGTH: 447
<212> TYPE: PRT
<213> ORGANISM: Artificial Sequence
<220> FEATURE:
<223> OTHER INFORMATION: L-glutamate dehydrogenase mutant 4 (A166G, V376A)

<400> SEQUENCE: 14

```
Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60
```

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Lys
            115                 120                 125

Gly Gly Ser Asp Phe Asp Pro Lys Gly Lys Ser Asp Leu Glu Ile Met
        130                 135                 140

Arg Phe Cys Gln Ser Phe Met Thr Glu Leu His Arg His Ile Gly Glu
145                 150                 155                 160

Tyr Arg Asp Val Pro Gly Gly Asp Ile Gly Val Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
    290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
        355                 360                 365

Lys Ala Ala Asn Ala Gly Gly Ala Ala Thr Ser Ala Leu Glu Met Gln
370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
        435                 440                 445

<210> SEQ ID NO 15
<211> LENGTH: 1341
<212> TYPE: DNA
<213> ORGANISM: Artificial Sequence
<220> FEATURE:

<223> OTHER INFORMATION: L-glutamate dehydrogenase mutant 4 (A166G, V376A)

<400> SEQUENCE: 15

```
atgaccgttg acgaacaggt ttctaactac tacgacatgc tgctgaaacg taacgctggt      60
gaaccggaat tccaccaggc tgttgctgaa gttctggaat ctctgaaaat cgttctggaa     120
aaagacccgc actacgctga ctacggtctg atccagcgtc tgtgcgaacc ggaacgtcag     180
ctgatcttcc gtgttccgtg ggttgacgac cagggtcagg ttcacgttaa ccgtggtttc     240
cgtgttcagt tcaactctgc tctgggtccg tacaaaggtg gtctgcgttt ccacccgtct     300
gttaacctgg gtatcgttaa attcctgggt ttcgaacaga tcttcaaaaa ctctctgacc     360
ggtctgccga tcggtggtgg taaaggtggt tctgacttcg acccgaaagg taaatctgac     420
ctggaaatca tgcgtttctg ccagtctttc atgaccgaac tgcaccgtca catcggtgaa     480
taccgtgacg ttccgggtgg tgacatcggt gttggtggtc gtgaaatcgg ttacctgttc     540
ggtcactacc gtcgtatggc taaccagcac gaatctggtg ttctgaccgg taaaggtctg     600
acctggggtg ttctctggt cgtaccgaa gctaccggtt acggttgcgt ttacttcgtt     660
tctgaaatga tcaaagctaa aggtgaatct atctctggtc agaaaatcat cgtttctggt     720
tctggtaacg ttgctaccta cgctatcgaa aaagctcagg aactgggtgc taccgttatc     780
ggtttctctg actcttctgg ttgggttcac accccgaacg tgttgacgt tgctaaactg     840
cgtgaaatca agaagttcg tcgtgctcgt gtttctgttt acgctgacga agttgaaggt     900
gctacctacc acaccgacgg ttctatctgg gacctgaaat cgacatcgc tctgccgtgc     960
gctacccaga cgaactgaa cggtgaaaac gctaaaaccc tggctgacaa cggttgccgt    1020
ttcgttgctg aaggtgctaa catgccgtct acccggaag ctgttgaagt tttccgtgaa    1080
cgtgacatcc gtttcggtcc gggtaaagct gctaacgctg tggtgctgc tacctctgct    1140
ctggaaatgc agcagaacgc ttctcgtgac tcttggtctt tcgaatacac cgacgaacgt    1200
ctgcaggtta tcatgaaaaa catcttcaaa acctgcgctg aaaccgctgc tgaatacggt    1260
cacgaaaacg actacgttgt tggtgctaac atcgctggtt tcaaaaaagt tgctgacgct    1320
atgctggctc agggtgttat c                                              1341
```

<210> SEQ ID NO 16
<211> LENGTH: 447
<212> TYPE: PRT
<213> ORGANISM: Artificial Sequence
<220> FEATURE:
<223> OTHER INFORMATION: L-glutamate dehydrogenase mutant 5 (A166G, V376S, T196V)

<400> SEQUENCE: 16

```
Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95
```

```
Phe His Pro Ser Val Asn Leu Gly Ile Val Lys Phe Leu Gly Phe Glu
            100                 105                 110
Gln Ile Phe Lys Asn Ser Leu Thr Gly Leu Pro Ile Gly Gly Gly Lys
        115                 120                 125
Gly Gly Ser Asp Phe Asp Pro Lys Gly Lys Ser Asp Leu Glu Ile Met
130                 135                 140
Arg Phe Cys Gln Ser Phe Met Thr Glu Leu His Arg His Ile Gly Glu
145                 150                 155                 160
Tyr Arg Asp Val Pro Gly Gly Asp Ile Gly Val Gly Gly Arg Glu Ile
                165                 170                 175
Gly Tyr Leu Phe Gly His Tyr Arg Arg Met Ala Asn Gln His Glu Ser
            180                 185                 190
Gly Val Leu Val Gly Lys Gly Leu Thr Trp Gly Gly Ser Leu Val Arg
        195                 200                 205
Thr Glu Ala Thr Gly Tyr Gly Cys Val Tyr Phe Val Ser Glu Met Ile
210                 215                 220
Lys Ala Lys Gly Glu Ser Ile Ser Gly Gln Lys Ile Ile Val Ser Gly
225                 230                 235                 240
Ser Gly Asn Val Ala Thr Tyr Ala Ile Glu Lys Ala Gln Glu Leu Gly
                245                 250                 255
Ala Thr Val Ile Gly Phe Ser Asp Ser Ser Gly Trp Val His Thr Pro
            260                 265                 270
Asn Gly Val Asp Val Ala Lys Leu Arg Glu Ile Lys Glu Val Arg Arg
        275                 280                 285
Ala Arg Val Ser Val Tyr Ala Asp Glu Val Glu Gly Ala Thr Tyr His
290                 295                 300
Thr Asp Gly Ser Ile Trp Asp Leu Lys Cys Asp Ile Ala Leu Pro Cys
305                 310                 315                 320
Ala Thr Gln Asn Glu Leu Asn Gly Glu Asn Ala Lys Thr Leu Ala Asp
                325                 330                 335
Asn Gly Cys Arg Phe Val Ala Glu Gly Ala Asn Met Pro Ser Thr Pro
            340                 345                 350
Glu Ala Val Glu Val Phe Arg Glu Arg Asp Ile Arg Phe Gly Pro Gly
        355                 360                 365
Lys Ala Ala Asn Ala Gly Gly Ser Ala Thr Ser Ala Leu Glu Met Gln
370                 375                 380
Gln Asn Ala Ser Arg Asp Ser Trp Ser Phe Glu Tyr Thr Asp Glu Arg
385                 390                 395                 400
Leu Gln Val Ile Met Lys Asn Ile Phe Lys Thr Cys Ala Glu Thr Ala
                405                 410                 415
Ala Glu Tyr Gly His Glu Asn Asp Tyr Val Val Gly Ala Asn Ile Ala
            420                 425                 430
Gly Phe Lys Lys Val Ala Asp Ala Met Leu Ala Gln Gly Val Ile
        435                 440                 445

<210> SEQ ID NO 17
<211> LENGTH: 1341
<212> TYPE: DNA
<213> ORGANISM: Artificial Sequence
<220> FEATURE:
<223> OTHER INFORMATION: L-glutamate dehydrogenase mutant 5 (A166G,
      V376S, T196V)

<400> SEQUENCE: 17
atgaccgttg acgaacaggt ttctaactac tacgacatgc tgctgaaacg taacgctggt    60
```

```
gaaccggaat tccaccaggc tgttgctgaa gttctggaat ctctgaaaat cgttctggaa      120
aaagacccgc actacgctga ctacggtctg atccagcgtc tgtgcgaacc ggaacgtcag      180
ctgatcttcc gtgttccgtg ggttgacgac cagggtcagg ttcacgttaa ccgtggtttc      240
cgtgttcagt tcaactctgc tctgggtccg tacaaaggtg gtctgcgttt ccacccgtct      300
gttaacctgg gtatcgttaa attcctgggt ttcgaacaga tcttcaaaaa ctctctgacc      360
ggtctgccga tcggtggtgg taaaggtggt tctgacttcg acccgaaagg taaatctgac      420
ctggaaatca tgcgtttctg ccagtctttc atgaccgaac tgcaccgtca catcggtgaa      480
taccgtgacg ttccgggtgg tgacatcggt gttggtggtc gtgaaatcgg ttacctgttc      540
ggtcactacc gtcgtatggc taaccagcac gaatctggtg ttctggttgg taaaggtctg      600
acctggggtg ttctctctgg tcgtaccgaa gctaccggtt acggttgcgt tacttcgtt       660 tctgaaatga tcaaagctaa aggtgaatct atctctggtc agaaaatcat cgtttctggt      720
tctggtaacg ttgctaccta cgctatcgaa aaagctcagg aactgggtgc taccgttatc      780
ggtttctctg actcttctgg ttgggttcac accccgaacg tgttgacgt tgctaaactg       840 cgtgaaatca agaagttcg tcgtgctcgt gtttctgttt acgctgacga agttgaaggt       900
gctacctacc acaccgacgg ttctatctgg gacctgaaat gcgacatcgc tctgccgtgc      960
gctacccaga cgaactgaa cggtgaaaac gctaaaaccc tggctgacaa cggttgccgt      1020
ttcgttgctg aaggtgctaa catgccgtct accccggaag ctgttgaagt tttccgtgaa     1080
cgtgacatcc gtttcggtcc gggtaaagct gctaacgctg gtggttctgc tacctctgct     1140
ctggaaatgc agcagaacgc ttctcgtgac tcttggtctt cgaatacac cgacgaacgt      1200 ctgcaggtta tcatgaaaaa catcttcaaa acctgcgctg aaaccgctgc tgaatacggt     1260
cacgaaaacg actacgttgt tggtgctaac atcgctggtt caaaaaagt tgctgacgct      1320 atgctggctc agggtgttat c                                              1341
```

<210> SEQ ID NO 18
<211> LENGTH: 447
<212> TYPE: PRT
<213> ORGANISM: Artificial Sequence
<220> FEATURE:
<223> OTHER INFORMATION: L-glutamate dehydrogenase mutant 6 (A166E, V376G)

<400> SEQUENCE: 18

```
Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125
```

Gly Gly Ser Asp Phe Asp Pro Lys Gly Lys Ser Asp Leu Glu Ile Met
            130                 135                 140

Arg Phe Cys Gln Ser Phe Met Thr Glu Leu His Arg His Ile Gly Glu
145                 150                 155                 160

Tyr Arg Asp Val Pro Glu Gly Asp Ile Gly Val Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
210                 215                 220

Lys Ala Lys Gly Glu Ser Ile Ser Gly Gln Lys Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
        355                 360                 365

Lys Ala Ala Asn Ala Gly Gly Gly Ala Thr Ser Ala Leu Glu Met Gln
370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
        435                 440                 445

<210> SEQ ID NO 19
<211> LENGTH: 1341
<212> TYPE: DNA
<213> ORGANISM: Artificial Sequence
<220> FEATURE:
<223> OTHER INFORMATION: L-glutamate dehydrogenase mutant 6 (A166E,
      V376G)

<400> SEQUENCE: 19
atgaccgttg acgaacaggt ttctaactac tacgacatgc tgctgaaacg taacgctggt      60
gaaccggaat ccaccaggc tgttgctgaa gttctggaat ctctgaaaat cgttctggaa      120
aaagacccgc actacgctga ctacggtctg atccagcgtc tgtgcgaacc ggaacgtcag      180
ctgatcttcc gtgttccgtg ggttgacgac cagggtcagg ttcacgttaa ccgtggtttc      240

-continued

```
cgtgttcagt tcaactctgc tctgggtccg tacaaaggtg gtctgcgttt ccacccgtct      300
gttaacctgg gtatcgttaa attcctgggt ttcgaacaga tcttcaaaaa ctctctgacc      360
ggtctgccga tcggtggtgg taaaggtggt tctgacttcg acccgaaagg taaatctgac      420
ctggaaatca tgcgtttctg ccagtctttc atgaccgaac tgcaccgtca catcggtgaa      480
taccgtgacg ttccggaagg tgacatcggt gttggtggtc gtgaaatcgg ttacctgttc      540
ggtcactacc gtcgtatggc taaccagcac gaatctggtg ttctgaccgg taaaggtctg      600
acctggggtg ttctctctgg tcgtaccgaa gctaccggtt acggttgcgt ttacttcgtt      660
tctgaaatga tcaaagctaa aggtgaatct atctctggtc agaaaatcat cgtttctggt      720
tctggtaacg ttgctaccta cgctatcgaa aaagctcagg aactgggtgc taccgttatc      780
ggtttctctg actcttctgg ttgggttcac accccgaacg tgttgacgt tgctaaactg       840 cgtgaaatca agaagttcg tcgtgctcgt gtttctgttt acgctgacga agttgaaggt       900
gctacctacc acaccgacgg ttctatctgg gacctgaaat gcgacatcgc tctgccgtgc      960
gctacccaga cgaactgaa cggtgaaaac gctaaaaccc tggctgacaa cggttgccgt      1020
ttcgttgctg aaggtgctaa catgccgtct ccccggaag ctgttgaagt tttccgtgaa      1080
cgtgacatcc gtttcggtcc gggtaaagct gctaacgctg gtggtggtgc tacctctgct     1140
ctggaaatgc agcagaacgc ttctcgtgac tcttggtctt cgaatacac cgacgaacgt      1200 ctgcaggtta tcatgaaaaa catcttcaaa acctgcgctg aaaccgctgc tgaatacggt      1260
cacgaaaacg actacgttgt tggtgctaac atcgctggtt tcaaaaagt tgctgacgct      1320 atgctggctc agggtgttat c                                                1341
```

<210> SEQ ID NO 20
<211> LENGTH: 447
<212> TYPE: PRT
<213> ORGANISM: Artificial Sequence
<220> FEATURE:
<223> OTHER INFORMATION: L-glutamate dehydrogenase mutant 7 (A166C, V376A)

<400> SEQUENCE: 20

```
Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160
```

Tyr Arg Asp Val Pro Cys Gly Asp Ile Gly Val Gly Arg Glu Ile
            165                 170                 175

Gly Tyr Leu Phe Gly His Tyr Arg Arg Met Ala Asn Gln His Glu Ser
        180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
    210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
    290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
        355                 360                 365

Lys Ala Ala Asn Ala Gly Gly Ala Ala Thr Ser Ala Leu Glu Met Gln
    370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
        435                 440                 445

<210> SEQ ID NO 21
<211> LENGTH: 1341
<212> TYPE: DNA
<213> ORGANISM: Artificial Sequence
<220> FEATURE:
<223> OTHER INFORMATION: L-glutamate dehydrogenase mutant 7 (A166C, V376A)

<400> SEQUENCE: 21
atgaccgttg acgaacaggt ttctaactac tacgacatgc tgctgaaacg taacgctggt      60
gaaccggaat ccaccaggc tgttgctgaa gttctggaat ctctgaaaat cgttctggaa      120
aaagacccgc actacgctga ctacggtctg atccagcgtc tgtgcgaacc ggaacgtcag      180
ctgatcttcc gtgttccgtg gttgacgac cagggtcagg ttcacgttaa ccgtggtttc      240
cgtgttcagt tcaactctgc tctgggtccg tacaaaggtg gtctgcgttt ccacccgtct      300
gttaacctgg gtatcgttaa attcctgggt ttcgaacaga tcttcaaaaa ctctctgacc      360
ggtctgccga tcggtggtgg taaaggtggt tctgacttcg acccgaaagg taaatctgac      420

```
ctggaaatca tgcgtttctg ccagtctttc atgaccgaac tgcaccgtca catcggtgaa    480
taccgtgacg ttccgtgcgg tgacatcggt gttggtggtc gtgaaatcgg ttacctgttc    540
ggtcactacc gtcgtatggc taaccagcac gaatctggtg ttctgaccgg taaaggtctg    600
acctggggtg ttctctggt tcgtaccgaa gctaccggtt acggttgcgt ttacttcgtt     660
tctgaaatga tcaaagctaa aggtgaatct atctctggtc agaaaatcat cgtttctggt    720
tctggtaacg ttgctaccta cgctatcgaa aaagctcagg aactgggtgc taccgttatc    780
ggtttctctg actcttctgg ttgggttcac accccgaacg tgttgacgt tgctaaactg      840 cgtgaaatca agaagttcg tcgtgctcgt gtttctgttt acgctgacga gttgaaggt       900 gctacctacc acaccgacgg ttctatctgg gacctgaaat gcgacatcgc tctgccgtgc    960
gctacccaga cgaactgaa cggtgaaaac gctaaaaccc tggctgacaa cggttgccgt     1020
ttcgttgctg aaggtgctaa catgccgtct accccggaag ctgttgaagt tttccgtgaa    1080
cgtgacatcc gttcggtcc gggtaaagct gctaacgctg tggtgctgc tacctctgct       1140 ctggaaatgc agcagaacgc ttctcgtgac tcttggtctt tcgaatacac cgacgaacgt    1200
ctgcaggtta tcatgaaaaa catcttcaaa acctgcgctg aaaccgctgc tgaatacggt    1260
cacgaaaacg actacgttgt tggtgctaac atcgctggtt tcaaaaaagt tgctgacgct    1320
atgctggctc agggtgttat c                                              1341
```

```
<210> SEQ ID NO 22
<211> LENGTH: 447
<212> TYPE: PRT
<213> ORGANISM: Artificial Sequence
<220> FEATURE:
<223> OTHER INFORMATION: L-glutamate dehydrogenase mutant 8 (A166G)

<400> SEQUENCE: 22

Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Gly Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190
```

Gly Val Leu Thr Gly Lys Gly Leu Thr Trp Gly Ser Leu Val Arg
        195                 200                 205

Thr Glu Ala Thr Gly Tyr Gly Cys Val Tyr Phe Val Ser Glu Met Ile
210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
    290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
        355                 360                 365

Lys Ala Ala Asn Ala Gly Gly Val Ala Thr Ser Ala Leu Glu Met Gln
    370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
        435                 440                 445

<210> SEQ ID NO 23
<211> LENGTH: 1341
<212> TYPE: DNA
<213> ORGANISM: Artificial Sequence
<220> FEATURE:
<223> OTHER INFORMATION: L-glutamate dehydrogenase mutant 8 (A166G)

<400> SEQUENCE: 23

| | | |
|---|---|---|
| atgaccgttg acgaacaggt ttctaactac tacgacatgc tgctgaaacg taacgctggt | 60 |
| gaaccggaat tccaccaggc tgttgctgaa gttctggaat ctctgaaaat cgttctggaa | 120 |
| aaagacccgc actacgctga ctacggtctg atccagcgtc tgtgcgaacc ggaacgtcag | 180 |
| ctgatcttcc gtgttccgtg ggttgacgac cagggtcagg ttcacgttaa ccgtggtttc | 240 |
| cgtgttcagt tcaactctgc tctgggtccg tacaaaggtg gtctgcgttt ccaccgtct | 300 |
| gttaacctgg gtatcgttaa attcctgggt ttcgaacaga tcttcaaaaa ctctctgacc | 360 |
| ggtctgccga cggtggtgg taaaggtggt tctgacttcg acccgaaagg taaatctgac | 420 |
| ctggaaatca tgcgtttctg ccagtctttc atgaccgaac tgcaccgtca catcggtgaa | 480 |
| taccgtgacg ttccgggtgg tgacatcggt gttggtggtc gtgaaatcgg ttacctgttc | 540 |
| ggtcactacc gtcgtatggc taaccagcac gaatctggtg ttctgaccgg taaaggtctg | 600 |
| acctggggtg ttctctctgg tcgtaccgaa gctaccggtt acggttgcgt ttacttcgtt | 660 |

-continued

```
tctgaaatga tcaaagctaa aggtgaatct atctctggtc agaaaatcat cgtttctggt    720
tctggtaacg ttgctaccta cgctatcgaa aaagctcagg aactgggtgc taccgttatc    780
ggtttctctg actcttctgg ttgggttcac accccgaacg tgttgacgt tgctaaactg     840 cgtgaaatca agaagttcg tcgtgctcgt gtttctgttt acgctgacga agttgaaggt     900
gctacctacc acaccgacgg ttctatctgg gacctgaaat gcgacatcgc tctgccgtgc    960
gctacccaga cgaactgaa cggtgaaaac gctaaaaccc tggctgacaa cggttgccgt    1020 tcgttgctg aaggtgctaa catgccgtct accccggaag ctgttgaagt tttccgtgaa    1080
cgtgacatcc gtttcggtcc gggtaaagct gctaacgctg tggtgttgc tacctctgct    1140 ctggaaatgc agcagaacgc ttctcgtgac tcttggtctt tcgaatacac cgacgaacgt    1200
ctgcaggtta tcatgaaaaa catcttcaaa acctgcgctg aaaccgctgc tgaatacggt    1260
cacgaaaacg actacgttgt tggtgctaac atcgctggtt tcaaaaaagt tgctgacgct    1320
atgctggctc agggtgttat c                                              1341
```

<210> SEQ ID NO 24
<211> LENGTH: 447
<212> TYPE: PRT
<213> ORGANISM: Artificial Sequence
<220> FEATURE:
<223> OTHER INFORMATION: L-glutamate dehydrogenase mutant 9 (A166G, V376G)

<400> SEQUENCE: 24

```
Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Gly Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
    210                 215                 220

Lys Ala Lys Gly Glu Ser Ile Ser Gly Gln Lys Ile Ile Val Ser Gly
```

```
                    225                 230                 235                 240

Ser Gly Asn Val Ala Thr Tyr Ala Ile Glu Lys Ala Gln Glu Leu Gly
                    245                 250                 255

Ala Thr Val Ile Gly Phe Ser Asp Ser Ser Gly Trp Val His Thr Pro
                260                 265                 270

Asn Gly Val Asp Val Ala Lys Leu Arg Glu Ile Lys Glu Val Arg Arg
            275                 280                 285

Ala Arg Val Ser Val Tyr Ala Asp Glu Val Glu Gly Ala Thr Tyr His
        290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
        355                 360                 365

Lys Ala Ala Asn Ala Gly Gly Gly Ala Thr Ser Ala Leu Glu Met Gln
    370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
        435                 440                 445

<210> SEQ ID NO 25
<211> LENGTH: 1341
<212> TYPE: DNA
<213> ORGANISM: Artificial Sequence
<220> FEATURE:
<223> OTHER INFORMATION: L-glutamate dehydrogenase mutant 9 (A166G,
      V376G)

<400> SEQUENCE: 25
atgaccgttg acgaacaggt ttctaactac tacgacatgc tgctgaaacg taacgctggt       60
gaaccggaat ccaccaggc tgttgctgaa gttctggaat ctctgaaaat cgttctggaa      120
aaagacccgc actacgctga ctacggtctg atccagcgtc tgtgcgaacc ggaacgtcag      180
ctgatcttcc gtgttccgtg ggttgacgac cagggtcagg ttcacgttaa ccgtggtttc      240
cgtgttcagt tcaactctgc tctgggtccg tacaaaggtg gtctgcgttt ccacccgtct      300
gttaacctgg gtatcgttaa attcctgggt ttcgaacaga tcttcaaaaa ctctctgacc      360
ggtctgccga tcggtggtgg taaaggtggt tctgacttcg acccgaaagg taaatctgac      420
ctggaaatca tgcgtttctg ccagtctttc atgaccgaac tgcaccgtca catcggtgaa      480
taccgtgacg ttccgggtgg tgacatcggt gttggtggtc gtgaaatcgg ttacctgttc      540
ggtcactacc gtcgtatggc taaccagcac gaatctggtg ttctgaccgg taaaggtctg      600
acctggggtg ttctctggt tcgtaccgaa gctaccggtt acggttgcgt ttacttcgtt      660
tctgaaatga tcaaagctaa aggtgaatct atctctggtc agaaaatcat cgtttctggt      720
tctggtaacg ttgctaccta cgctatcgaa aaagctcagg aactgggtgc taccgttatc      780
ggtttctctg actcttctgg ttgggttcac accccgaacg gtgttgacgt tgctaaactg      840
```

```
cgtgaaatca aagaagtttcg tcgtgctcgt gtttctgttt acgctgacga agttgaaggt    900
gctacctacc acaccgacgg ttctatctgg gacctgaaat gcgacatcgc tctgccgtgc    960
gctacccaga acgaactgaa cgtgaaaaac gctaaaaccc tggctgacaa cggttgccgt   1020
ttcgttgctg aaggtgctaa catgccgtct accccggaag ctgttgaagt tttccgtgaa   1080
cgtgacatcc gtttcggtcc gggtaaagct gctaacgctg gtggtggtgc tacctctgct   1140
ctggaaatgc agcagaacgc ttctcgtgac tcttggtctt tcgaatacac cgacgaacgt   1200
ctgcaggtta tcatgaaaaa catcttcaaa acctgcgctg aaaccgctgc tgaatacggt   1260
cacgaaaacg actacgttgt tggtgctaac atcgctggtt tcaaaaaagt tgctgacgct   1320
atgctggctc agggtgttat c                                             1341
```

<210> SEQ ID NO 26
<211> LENGTH: 447
<212> TYPE: PRT
<213> ORGANISM: Artificial Sequence
<220> FEATURE:
<223> OTHER INFORMATION: L-glutamate dehydrogenase mutant 10 (A166G, V376E)

<400> SEQUENCE: 26

```
Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Gly Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
    210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
```

```
            260                 265                 270
Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
        290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
                340                 345                 350

Glu Ala Val Glu Val Phe Arg Glu Arg Asp Ile Arg Phe Gly Pro Gly
            355                 360                 365

Lys Ala Ala Asn Ala Gly Gly Glu Ala Thr Ser Ala Leu Glu Met Gln
        370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
                420                 425                 430

Gly Phe Lys Lys Val Ala Asp Ala Met Leu Ala Gln Gly Val Ile
        435                 440                 445

<210> SEQ ID NO 27
<211> LENGTH: 1341
<212> TYPE: DNA
<213> ORGANISM: Artificial Sequence
<220> FEATURE:
<223> OTHER INFORMATION: L-glutamate dehydrogenase mutant 10 (A166G,
      V376E)

<400> SEQUENCE: 27
atgaccgttg acgaacaggt ttctaactac tacgacatgc tgctgaaacg taacgctggt      60
gaaccggaat ccaccaggc tgttgctgaa gttctggaat ctctgaaaat cgttctggaa      120
aaagacccgc actacgctga ctacggtctg atccagcgtc tgtgcgaacc ggaacgtcag      180
ctgatcttcc gtgttccgtg ggttgacgac caggtcagg ttcacgttaa ccgtggtttc      240
cgtgttcagt tcaactctgc tctgggtccg tacaaaggtg gtctgcgttt ccacccgtct      300
gttaacctgg gtatcgttaa attcctgggt ttcgaacaga tcttcaaaaa ctctctgacc      360
ggtctgccga tcggtggtgg taaaggtggt tctgacttcg acccgaaagg taaatctgac      420
ctggaaatca tgcgtttctg ccagtctttc atgaccgaac tgcaccgtca catcggtgaa      480
taccgtgacg ttccgggtgg tgacatcggt gttggtggtc gtgaaatcgg ttacctgttc      540
ggtcactacc gtcgtatggc taaccagcac gaatctggtg ttctgaccgg taaggtctg      600 acctggggtg ttctctctgg tcgtaccgaa gctaccggtt acggttgcgt ttacttcgtt      660
tctgaaatga tcaaagctaa aggtgaatct atctctggtc agaaaatcat cgtttctggt      720
tctggtaacg ttgctaccta cgctatcgaa aaagctcagg aactgggtgc taccgttatc      780
ggtttctctg actcttctgg ttgggttcac accccgaacg tgttgacgt tgctaaactg      840 cgtgaaatca agaagttcg tcgtgctcgt gtttctgttt acgctgacga agttgaaggt      900
gctacctacc acaccgacgg ttctatctgg gacctgaaat gcgacatcgc tctgccgtgc      960
gctacccaga acgaactgaa cggtgaaaac gctaaaaccc tggctgacaa cggttgccgt     1020
```

```
ttcgttgctg aaggtgctaa catgccgtct accccggaag ctgttgaagt tttccgtgaa    1080
cgtgacatcc gtttcggtcc gggtaaagct gctaacgctg tggtgaagc tacctctgct     1140 ctggaaatgc agcagaacgc ttctcgtgac tcttggtctt tcgaatacac cgacgaacgt    1200
ctgcaggtta tcatgaaaaa catcttcaaa acctgcgctg aaaccgctgc tgaataccgt    1260
cacgaaaacg actacgttgt tggtgctaac atcgctggtt tcaaaaaagt tgctgacgct    1320
atgctggctc agggtgttat c                                               1341
```

<210> SEQ ID NO 28
<211> LENGTH: 447
<212> TYPE: PRT
<213> ORGANISM: Artificial Sequence
<220> FEATURE:
<223> OTHER INFORMATION: L-glutamate dehydrogenase mutant 11 (A166G, V376Q)

<400> SEQUENCE: 28

```
Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Gly Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
    210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
```

```
                    290                 295                 300
Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
                340                 345                 350

Glu Ala Val Glu Val Phe Arg Glu Arg Asp Ile Arg Phe Gly Pro Gly
            355                 360                 365

Lys Ala Ala Asn Ala Gly Gly Gln Ala Thr Ser Ala Leu Glu Met Gln
        370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
                420                 425                 430

Gly Phe Lys Lys Val Ala Asp Ala Met Leu Ala Gln Gly Val Ile
            435                 440                 445

<210> SEQ ID NO 29
<211> LENGTH: 1341
<212> TYPE: DNA
<213> ORGANISM: Artificial Sequence
<220> FEATURE:
<223> OTHER INFORMATION: L-glutamate dehydrogenase mutant 11 (A166G,
      V376Q)

<400> SEQUENCE: 29
atgaccgttg acgaacaggt ttctaactac tacgacatgc tgctgaaacg taacgctggt      60
gaaccggaat ccaccaggc tgttgctgaa gttctggaat ctctgaaaat cgttctggaa     120
aaagacccgc actacgctga ctacggtctg atccagcgtc tgtgcgaacc ggaacgtcag     180
ctgatcttcc gtgttccgtg ggttgacgac cagggtcagg ttcacgttaa ccgtggtttc     240
cgtgttcagt tcaactctgc tctgggtccg tacaaaggtg gtctgcgttt ccacccgtct     300
gttaacctgg gtatcgttaa attcctgggt ttcgaacaga tcttcaaaaa ctctctgacc     360
ggtctgccga cggtggtgg taaaggtggt tctgacttcg acccgaaagg taaatctgac     420
ctggaaatca tgcgtttctg ccagtctttc atgaccgaac tgcaccgtca catcggtgaa     480
taccgtgacg ttccgggtgg tgacatcggt gttggtggtc gtgaaatcgg ttacctgttc     540
ggtcactacc gtcgtatggc taaccagcac gaatctggtg ttctgaccgg taaaggtctg     600 acctgggggtg ttctctctggt tcgtaccgaa gctaccggtt acggttgcgt ttacttcgtt     660
tctgaaatga tcaaagctaa aggtgaatct atctctggtc agaaaatcat cgtttctggt     720
tctggtaacg ttgctaccta cgctatcgaa aaagctcagg aactgggtgc taccgttatc     780
ggtttctctg actcttctgg ttgggttcac accccgaacg tgttgacgt tgctaaactg     840 cgtgaaatca agaagttcg tcgtgctcgt gtttctgttt acgctgacga agttgaaggt     900
gctacctacc acaccgacgg ttctatctgg gacctgaaat gcgacatcgc tctgccgtgc     960
gctacccaga cgaactgaa cggtgaaaac gctaaaccc tggctgacaa cggttgccgt    1020 tcgttgctg aaggtgctaa catgccgtct accccggaag ctgttgaagt tttccgtgaa    1080
cgtgacatcc gtttcggtcc gggtaaagct gctaacgctg gtggtcaggc tacctctgct    1140
ctggaaatgc agcagaacgc ttctcgtgac tcttggtctt tcgaatacac cgacgaacgt    1200
```

```
ctgcaggtta tcatgaaaaa catcttcaaa acctgcgctg aaaccgctgc tgaatacggt   1260
cacgaaaacg actacgttgt tggtgctaac atcgctggtt tcaaaaaagt tgctgacgct   1320
atgctggctc agggtgttat c                                             1341
```

<210> SEQ ID NO 30
<211> LENGTH: 447
<212> TYPE: PRT
<213> ORGANISM: Artificial Sequence
<220> FEATURE:
<223> OTHER INFORMATION: L-glutamate dehydrogenase mutant 12 (A166G, V376S, T196S)

<400> SEQUENCE: 30

```
Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Gly Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Ser Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
    210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
    290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
```

|  | 325 |  |  |  |  | 330 |  |  |  |  | 335 |  |
|---|---|---|---|---|---|---|---|---|---|---|---|---|
| Asn | Gly | Cys | Arg | Phe | Val | Ala | Glu | Gly | Ala | Asn | Met | Pro | Ser | Thr | Pro |

Asn Gly Cys Arg Phe Val Ala Glu Gly Ala Asn Met Pro Ser Thr Pro
                325                 330                 335

Glu Ala Val Glu Val Phe Arg Glu Arg Asp Ile Arg Phe Gly Pro Gly
            340                 345                 350

Lys Ala Asn Ala Gly Gly Ser Ala Thr Ser Ala Leu Glu Met Gln
    355                 360                 365

Lys Ala Asn Ala Gly Gly Ser Ala Thr Ser Ala Leu Glu Met Gln
        370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
            405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
        435                 440                 445

<210> SEQ ID NO 31
<211> LENGTH: 1341
<212> TYPE: DNA
<213> ORGANISM: Artificial Sequence
<220> FEATURE:
<223> OTHER INFORMATION: L-glutamate dehydrogenase mutant 12 (A166G,
      V376S, T196S)

<400> SEQUENCE: 31

```
atgaccgttg acgaacaggt ttctaactac tacgacatgc tgctgaaacg taacgctggt      60
gaaccggaat tccaccaggc tgttgctgaa gttctggaat ctctgaaaat cgttctggaa     120
aaagacccgc actacgctga ctacggtctg atccagcgtc tgtgcgaacc ggaacgtcag     180
ctgatcttcc gtgttccgtg ggttgacgac cagggtcagg ttcacgttaa ccgtggtttc     240
cgtgttcagt tcaactctgc tctgggtccg tacaaaggtg gtctgcgttt ccacccgtct     300
gttaacctgg gtatcgttaa attcctgggt ttcgaacaga tcttcaaaaa ctctctgacc     360
ggtctgccga tcggtggtgg taaaggtggt tctgacttcg acccgaaagg taaatctgac     420
ctggaaatca tgcgtttctg ccagtctttc atgaccgaac tgcaccgtca catcggtgaa     480
taccgtgacg ttccgggtgg tgacatcggt gttggtggtc gtgaaatcgg ttacctgttc     540
ggtcactacc gtcgtatggc taaccagcac gaatctggtg ttctgtctgg taaaggtctg     600
acctggggtg ttctctggt cgtaccgaa gctaccggtt acggttgcgt ttacttcgtt     660
tctgaaatga tcaaagctaa aggtgaatct atctctggtc agaaaatcat cgtttctggt     720
tctggtaacg ttgctaccta cgctatcgaa aaagctcagg aactgggtgc taccgttatc     780
ggttctctg actcttctgg ttgggttcac accccgaacg tgttgacgt tgctaaactg     840
cgtgaaatca agaagttcg tcgtgctcgt gtttctgttt acgctgacga agttgaaggt     900
gctacctacc acaccgacgg ttctatctgg gacctgaaat gcgacatcgc tctgccgtgc     960
gctacccaga cgaactgaa cggtgaaaac gctaaacccc tggctgacaa cggttgccgt    1020
ttcgttgctg aaggtgctaa catgccgtct accccggaag ctgttgaagt tttccgtgaa    1080
cgtgacatcc gttcggtcc gggtaaagct gctaacgctg gtggttctgc tacctctgct    1140
ctggaaatgc agcagaacgc ttctcgtgac tcttggtctt tcgaatacac cgacgaacgt    1200
ctgcaggtta tcatgaaaaa catcttcaaa acctgcgctg aaaccgctgc tgaatacggt    1260
cacgaaaacg actacgttgt tggtgctaac atcgctggtt tcaaaaagt tgctgacgct    1320
atgctggctc agggtgttat c                                              1341
```

<210> SEQ ID NO 32
<211> LENGTH: 447
<212> TYPE: PRT
<213> ORGANISM: Artificial Sequence
<220> FEATURE:
<223> OTHER INFORMATION: L-glutamate dehydrogenase mutant 13 (A166T)

<400> SEQUENCE: 32

```
Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Thr Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
    210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
    290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
        355                 360                 365
```

```
Lys Ala Asn Ala Gly Gly Val Ala Thr Ser Ala Leu Glu Met Gln
    370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
                420                 425                 430

Gly Phe Lys Lys Val Ala Asp Ala Met Leu Ala Gln Gly Val Ile
                435                 440                 445

<210> SEQ ID NO 33
<211> LENGTH: 1341
<212> TYPE: DNA
<213> ORGANISM: Artificial Sequence
<220> FEATURE:
<223> OTHER INFORMATION: L-glutamate dehydrogenase mutant 13 (A166T)

<400> SEQUENCE: 33
atgaccgttg acgaacaggt ttctaactac tacgacatgc tgctgaaacg taacgctggt      60
gaaccggaat tccaccaggc tgttgctgaa gttctggaat ctctgaaaat cgttctggaa     120
aaagacccgc tactgctga ctacggtctg atccagcgtc tgtgcgaacc ggaacgtcag     180
ctgatcttcc gtgttccgtg ggttgacgac cagggtcagg ttcacgttaa ccgtggtttc     240
cgtgttcagt tcaactctgc tctgggtccg tacaaaggtg tctgcgtttt ccacccgtct     300
gttaacctgg gtatcgttaa attcctgggt ttcgaacaga tcttcaaaaa ctctctgacc     360
ggtctgccga tcggtggtgg taaaggtggt tctgacttcg acccgaaagg taaatctgac     420
ctggaaatca tgcgtttctg ccagtctttc atgaccgaac tgcaccgtca catcggtgaa     480
taccgtgacg ttccgaccgg tgacatcggt gttggtggtc gtgaaatcgg ttacctgttc     540
ggtcactacc gtcgtatggc taaccagcac gaatctggtg ttctgaccgg taaaggtctg     600
acctggggtg ttctctggt cgtaccgaa gctaccggtt acggttgcgt ttacttcgtt     660
tctgaaatga tcaaagctaa aggtgaatct atctctggtc agaaaatcat cgtttctggt     720
tctggtaacg ttgctaccta cgctatcgaa aaagctcagg aactgggtgc taccgttatc     780
ggtttctctg actcttctgg ttgggttcac accccgaacg tgttgacgt tgctaaactg     840
cgtgaaatca agaagttcg tcgtgctcgt gtttctgttt acgctgacga agttgaaggt     900
gctacctacc acaccgacgg ttctatctgg gacctgaaat cgacatcgc tctgccgtgc     960
gctacccaga cgaactgaa cggtgaaaac gctaaaccc tggctgacaa cggttgccgt    1020
ttcgttgctg aaggtgctaa catgccgtct accccggaag ctgttgaagt tttccgtgaa    1080
cgtgacatcc gtttcggtcc gggtaaagct gctaacgctg tggtgttgc tacctctgct    1140
ctggaaatgc agcagaacgc ttctcgtgac tcttggtctt tcgaatacac cgacgaacgt    1200
ctgcaggtta tcatgaaaaa catcttcaaa acctgcgctg aaaccgctgc tgaatacggt    1260
cacgaaaacg actacgttgt tggtgctaac atcgctggtt tcaaaaaagt tgctgacgct    1320
atgctggctc agggtgttat c                                              1341

<210> SEQ ID NO 34
<211> LENGTH: 447
<212> TYPE: PRT
<213> ORGANISM: Artificial Sequence
<220> FEATURE:
<223> OTHER INFORMATION: L-glutamate dehydrogenase mutant 14 (A166G,
```

V376S)

<400> SEQUENCE: 34

| | | | | | | | | | | | | | | |
|---|---|---|---|---|---|---|---|---|---|---|---|---|---|---|
| Met | Thr | Val | Asp | Glu | Gln | Val | Ser | Asn | Tyr | Tyr | Asp | Met | Leu | Leu | Lys |
| 1 | | | | 5 | | | | | 10 | | | | | 15 | |

Arg Asn Ala Gly Glu Pro Glu Phe His Gln Ala Val Ala Glu Val Leu
           20                  25                  30

Glu Ser Leu Lys Ile Val Leu Glu Lys Asp Pro His Tyr Ala Asp Tyr
         35                  40                  45

Gly Leu Ile Gln Arg Leu Cys Glu Pro Glu Arg Gln Leu Ile Phe Arg
 50                  55                  60

Val Pro Trp Val Asp Asp Gln Gly Gln Val His Val Asn Arg Gly Phe
 65                  70                  75                  80

Arg Val Gln Phe Asn Ser Ala Leu Gly Pro Tyr Lys Gly Gly Leu Arg
                 85                  90                  95

Phe His Pro Ser Val Asn Leu Gly Ile Val Lys Phe Leu Gly Phe Glu
             100                 105                 110

Gln Ile Phe Lys Asn Ser Leu Thr Gly Leu Pro Ile Gly Gly Gly Lys
         115                 120                 125

Gly Gly Ser Asp Phe Asp Pro Lys Gly Lys Ser Asp Leu Glu Ile Met
130                 135                 140

Arg Phe Cys Gln Ser Phe Met Thr Glu Leu His Arg His Ile Gly Glu
145                 150                 155                 160

Tyr Arg Asp Val Pro Gly Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
    210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
    290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
        355                 360                 365

Lys Ala Ala Asn Ala Gly Gly Ser Ala Thr Ser Ala Leu Glu Met Gln
    370                 375                 380

Gln Asn Ala Ser Arg Asp Ser Trp Ser Phe Glu Tyr Thr Asp Glu Arg
385                 390                 395                 400

-continued

Leu Gln Val Ile Met Lys Asn Ile Phe Lys Thr Cys Ala Glu Thr Ala
                    405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
        435                 440                 445

<210> SEQ ID NO 35
<211> LENGTH: 1341
<212> TYPE: DNA
<213> ORGANISM: Artificial Sequence
<220> FEATURE:
<223> OTHER INFORMATION: L-glutamate dehydrogenase mutant 14 (A166G, V376S)

<400> SEQUENCE: 35

```
atgaccgttg acgaacaggt ttctaactac tacgacatgc tgctgaaacg taacgctggt      60
gaaccggaat ccaccaggc tgttgctgaa gttctggaat ctctgaaaat cgttctggaa      120
aaagacccgc actacgctga ctacggtctg atccagcgtc tgtgcgaacc ggaacgtcag      180
ctgatcttcc gtgttccgtg ggttgacgac cagggtcagg ttcacgttaa ccgtggtttc      240
cgtgttcagt tcaactctgc tctgggtccg tacaaaggtg tctgcgtttt ccacccgtct      300
gttaacctgg gtatcgttaa attcctgggt ttcgaacaga tcttcaaaaa ctctctgacc      360
ggtctgccga tcggtggtgg taaaggtggt tctgacttcg acccgaaagg taatctgac      420
ctggaaatca tgcgtttctg ccagtctttc atgaccgaac tgcaccgtca tcggtgaa       480
taccgtgacg ttccgggtgg tgacatcggt gttggtggtc gtgaaatcgg ttacctgttc      540
ggtcactacc gtcgtatggc taaccagcac gaatctggtg ttctgaccgg taaaggtctg      600
acctggggtg ttctctctgg tcgtaccgaa gctaccggtt acggttgcgt ttacttcgtt      660
tctgaaatga tcaaagctaa aggtgaatct atctctggtc agaaaatcat cgtttctggt      720
tctggtaacg ttgctaccta cgctatcgaa aaagctcagg aactgggtgc taccgttatc      780
ggtttctctg actcttctgg ttgggttcac accccgaacg tgttgacgt tgctaaactg      840
cgtgaaatca agaagttcg tcgtgctcgt gtttctgttt acgctgacga agttgaaggt      900
gctacctacc acaccgacgg ttctatctgg gacctgaaat gcgacatcgc tctgccgtgc      960
gctacccaga cgaactgaa cggtgaaaac gctaaaccc tggctgacaa cggttgccgt      1020
ttcgttgctg aaggtgctaa catgccgtct accccggaag ctgttgaagt tttccgtgaa      1080
cgtgacatcc gtttcggtcc gggtaaagct gctaacgctg gtggttctgc tacctctgct      1140
ctggaaatgc agcagaacgc ttctcgtgac tcttggtctt cgaatacac cgacgaacgt      1200
ctgcaggtta tcatgaaaaa catcttcaaa acctgcgctg aaaccgctgc tgaatacggt      1260
cacgaaaacg actacgttgt tggtgctaac atcgctggtt tcaaaaagt tgctgacgct      1320
atgctggctc agggtgttat c                                             1341
```

<210> SEQ ID NO 36
<211> LENGTH: 447
<212> TYPE: PRT
<213> ORGANISM: Artificial Sequence
<220> FEATURE:
<223> OTHER INFORMATION: L-glutamate dehydrogenase mutant 15 (A166G, V376S, T196C)

<400> SEQUENCE: 36

Met Thr Val Asp Glu Gln Val Ser Asn Tyr Tyr Asp Met Leu Leu Lys
1               5                   10                  15

-continued

```
Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
 50                  55                  60

Val Pro Trp Val Asp Asp Gln Gly Gln Val His Val Asn Arg Gly Phe
 65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
            115                 120                 125

Gly Gly Ser Asp Phe Asp Pro Lys Gly Lys Ser Asp Leu Glu Ile Met
130                 135                 140

Arg Phe Cys Gln Ser Phe Met Thr Glu Leu His Arg His Ile Gly Glu
145                 150                 155                 160

Tyr Arg Asp Val Pro Gly Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Cys Gly Lys Gly Leu Thr Trp Gly Gly Ser Leu Val Arg
            195                 200                 205

Thr Glu Ala Thr Gly Tyr Gly Cys Val Tyr Phe Val Ser Glu Met Ile
210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
            275                 280                 285

Ala Arg Val Ser Val Tyr Ala Asp Glu Val Glu Gly Ala Thr Tyr His
            290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
            355                 360                 365

Lys Ala Ala Asn Ala Gly Gly Ser Ala Thr Ser Ala Leu Glu Met Gln
            370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
            420                 425                 430
```

Gly Phe Lys Lys Val Ala Asp Ala Met Leu Ala Gln Gly Val Ile
        435                 440                 445

<210> SEQ ID NO 37
<211> LENGTH: 1341
<212> TYPE: DNA
<213> ORGANISM: Artificial Sequence
<220> FEATURE:
<223> OTHER INFORMATION: L-glutamate dehydrogenase mutant 15 (A166G,
      V376S, T196C)

<400> SEQUENCE: 37

```
atgaccgttg acgaacaggt ttctaactac tacgacatgc tgctgaaacg taacgctggt        60
gaaccggaat tccaccaggc tgttgctgaa gttctggaat ctctgaaaat cgttctggaa       120
aaagacccgc actacgctga ctacggtctg atccagcgtc tgtgcgaacc ggaacgtcag       180
ctgatcttcc gtgttccgtg ggttgacgac cagggtcagg ttcacgttaa ccgtggtttc       240
cgtgttcagt tcaactctgc tctgggtccg tacaaaggtg gtctgcgttt ccacccgtct       300
gttaacctgg gtatcgttaa attcctgggt ttcgaacaga tcttcaaaaa ctctctgacc       360
ggtctgccga tcggtggtgg taaaggtggt tctgacttcg acccgaaagg taaatctgac       420
ctggaaatca tgcgtttctg ccagtctttc atgaccgaac tgcaccgtca catcggtgaa       480
taccgtgacg ttccgggtgg tgacatcggt gttggtggtc gtgaaatcgg ttacctgttc       540
ggtcactacc gtcgtatggc taaccagcac gaatctggtt tctgtgcgg taaaggtctg       600
acctggggtg ttctctggt cgtaccgaa gctaccggtt acggttgcgt tacttcgtt        660
tctgaaatga tcaaagctaa aggtgaatct atctctggtc agaaaatcat cgtttctggt       720
tctggtaacg ttgctaccta cgctatcgaa aaagctcagg aactgggtgc taccgttatc       780
ggtttctctg actcttctgg ttgggttcac accccgaacg tgttgacgt tgctaaactg        840
cgtgaaatca agaagttcg tcgtgctcgt gtttctgttt acgctgacga agttgaaggt       900
gctacctacc acaccgacgg ttctatctgg gacctgaaat cgacatcgc tctgccgtgc       960
gctacccaga cgaactgaa cggtgaaaac gctaaaaccc tggctgacaa cggttgccgt      1020
ttcgttgctg aaggtgctaa catgccgtct accccggaag ctgttgaagt ttccgtgaa       1080
cgtgacatcc gtttcggtcc gggtaaagct gctaacgctg gtggttctgc tacctctgct      1140
ctggaaatgc agcagaacgc ttctcgtgac tcttggtctt cgaatacac cgacgaacgt      1200
ctgcaggtta tcatgaaaaa catcttcaaa acctgcgctg aaaccgctgc tgaatacggt      1260
cacgaaaacg actacgttgt tggtgctaac atcgctggtt tcaaaaaagt tgctgacgct      1320
atgctggctc agggtgttat c                                                1341
```

<210> SEQ ID NO 38
<211> LENGTH: 447
<212> TYPE: PRT
<213> ORGANISM: Artificial Sequence
<220> FEATURE:
<223> OTHER INFORMATION: L-glutamate dehydrogenase mutant 16 (A166H,
      V376S)

<400> SEQUENCE: 38

Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
 50                  55                  60

Val Pro Trp Val Asp Asp Gln Gly Gln Val His Val Asn Arg Gly Phe
 65                  70                  75                  80

Arg Val Gln Phe Asn Ser Ala Leu Gly Pro Tyr Lys Gly Gly Leu Arg
                 85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
130                 135                 140

Arg Phe Cys Gln Ser Phe Met Thr Glu Leu His Arg His Ile Gly Glu
145                 150                 155                 160

Tyr Arg Asp Val Pro His Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
        355                 360                 365

Lys Ala Ala Asn Ala Gly Gly Ser Ala Thr Ser Ala Leu Glu Met Gln
370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
        435                 440                 445

<210> SEQ ID NO 39
<211> LENGTH: 1341

```
<212> TYPE: DNA
<213> ORGANISM: Artificial Sequence
<220> FEATURE:
<223> OTHER INFORMATION: L-glutamate dehydrogenase mutant 16 (A166H,
      V376S)

<400> SEQUENCE: 39
atgaccgttg acgaacaggt ttctaactac tacgacatgc tgctgaaacg taacgctggt      60
gaaccggaat tccaccaggc tgttgctgaa gttctggaat ctctgaaaat cgttctggaa     120
aaagacccgc actacgctga ctacggtctg atccagcgtc tgtgcgaacc ggaacgtcag     180
ctgatcttcc gtgttccgtg ggttgacgac cagggtcagg ttcacgttaa ccgtggtttc     240
cgtgttcagt tcaactctgc tctgggtccg tacaaaggtg gtctgcgttt ccacccgtct     300
gttaacctgg gtatcgttaa attcctgggt ttcaacaga tcttcaaaaa ctctctgacc      360
ggtctgccga tcggtggtgg taaaggtggt tctgacttcg acccgaaagg taaatctgac     420
ctggaaatca tgcgtttctg ccagtctttc atgaccgaac tgcaccgtca catcggtgaa     480
taccgtgacg ttccgcacgg tgacatcggt gttggtggtc gtgaaatcgg ttacctgttc     540
ggtcactacc gtcgtatggc taaccagcac gaatctggtg ttctgaccgg taaaggtctg     600
acctggggtg gttctctggt tcgtaccgaa gctaccggtt acggttgcgt ttacttcgtt     660
tctgaaatga tcaaagctaa aggtgaatct atctctggtc agaaaatcat cgtttctggt     720
tctggtaacg ttgctaccta cgctatcgaa aaagctcagg aactgggtgc taccgttatc     780
ggtttctctg actcttctgg ttgggttcac accccgaacg gtgttgacgt tgctaaactg     840
cgtgaaatca agaagttcg tcgtgctcgt gtttctgttt acgctgacga agttgaaggt      900
gctacctacc acaccgacgg ttctatctgg gacctgaaat gcgacatcgc tctgccgtgc     960
gctacccaga cgaactgaa cggtgaaaac gctaaaaccc tggctgacaa cggttgccgt    1020
ttcgttgctg aaggtgctaa catgccgtct accccggaag ctgttgaagt tttccgtgaa    1080
cgtgacatcc gtttcggtcc gggtaaagct gctaacgctg gtggttctgc tacctctgct    1140
ctggaaatgc agcagaacgc ttctcgtgac tcttggtctt tcgaatacac cgacgaacgt    1200
ctgcaggtta tcatgaaaaa catcttcaaa acctgcgctg aaaccgctgc tgaatacggt    1260
cacgaaaacg actacgttgt tggtgctaac atcgctggtt tcaaaaaagt tgctgacgct    1320
atgctggctc agggtgttat c                                              1341
```